(12) United States Patent
Thompson et al.

(10) Patent No.: US 6,547,784 B1
(45) Date of Patent: Apr. 15, 2003

(54) SYSTEM AND METHOD FOR PLACEMENT OF A SURGICAL INSTRUMENT IN A BODY CAVITY

(75) Inventors: Todd Thompson, San Jose, CA (US); Lauren K. Lundquist, Morgan Hill, CA (US)

(73) Assignee: Ethicon, Inc., Somerville, NJ (US)

( * ) Notice: Subject to any disclaimer, the term of this patent is extended or adjusted under 35 U.S.C. 154(b) by 88 days.

(21) Appl. No.: 09/603,152

(22) Filed: Jun. 23, 2000

(51) Int. Cl.[7] .............................................. A61B 18/18
(52) U.S. Cl. ........................................... 606/21; 606/20
(58) Field of Search ............................... 606/20–26, 41; 607/122

(56) References Cited

U.S. PATENT DOCUMENTS

| 3,924,628 A | * | 12/1975 | Droegemueller et al. ..... 606/21 |
| 4,016,867 A | | 4/1977 | King et al. |
| 4,121,572 A | | 10/1978 | Krzeminski |
| 4,204,548 A | | 5/1980 | Kurz |
| 4,685,474 A | | 8/1987 | Kurz et al. |
| 4,764,845 A | | 8/1988 | Artus |
| 4,873,986 A | | 10/1989 | Wallace |
| 5,275,595 A | | 1/1994 | Dobak, III |
| 5,500,012 A | * | 3/1996 | Brucker et al. ................ 604/22 |
| 5,520,682 A | | 5/1996 | Baust et al. |
| 5,647,868 A | | 7/1997 | Chinn |
| 5,702,438 A | * | 12/1997 | Avitall ......................... 600/374 |
| 5,782,899 A | * | 7/1998 | Imran .......................... 600/374 |
| 5,868,735 A | * | 2/1999 | Lafontaine .................... 606/21 |
| 6,009,877 A | * | 1/2000 | Edwards ...................... 128/898 |

* cited by examiner

Primary Examiner—Michael Peffley

(57) ABSTRACT

A cryoprobe sheath has at least one positioning element that deploys and retracts to permit the insertion of the cryoprobe into a uterus without using ultrasound or fluoroscopy. Deployment of the positioning element(s) positions the cryoprobe within the uterus permitting even cooling to facilitate cryoablation. The positioning element(s) and sheath may be withdrawn either after tacking the cryoprobe in position by a momentary activation or after a complete activation cycle, with each positioning element pulling through frozen medium in its own track. A guide and filler tube may be employed to infuse the correct quantity of thermally conductive medium into the uterus for cryoablation. The guide and filler tube allows fluid volume and pressure to be measured to avoid inadvertently breaching the uterine wall.

27 Claims, 16 Drawing Sheets

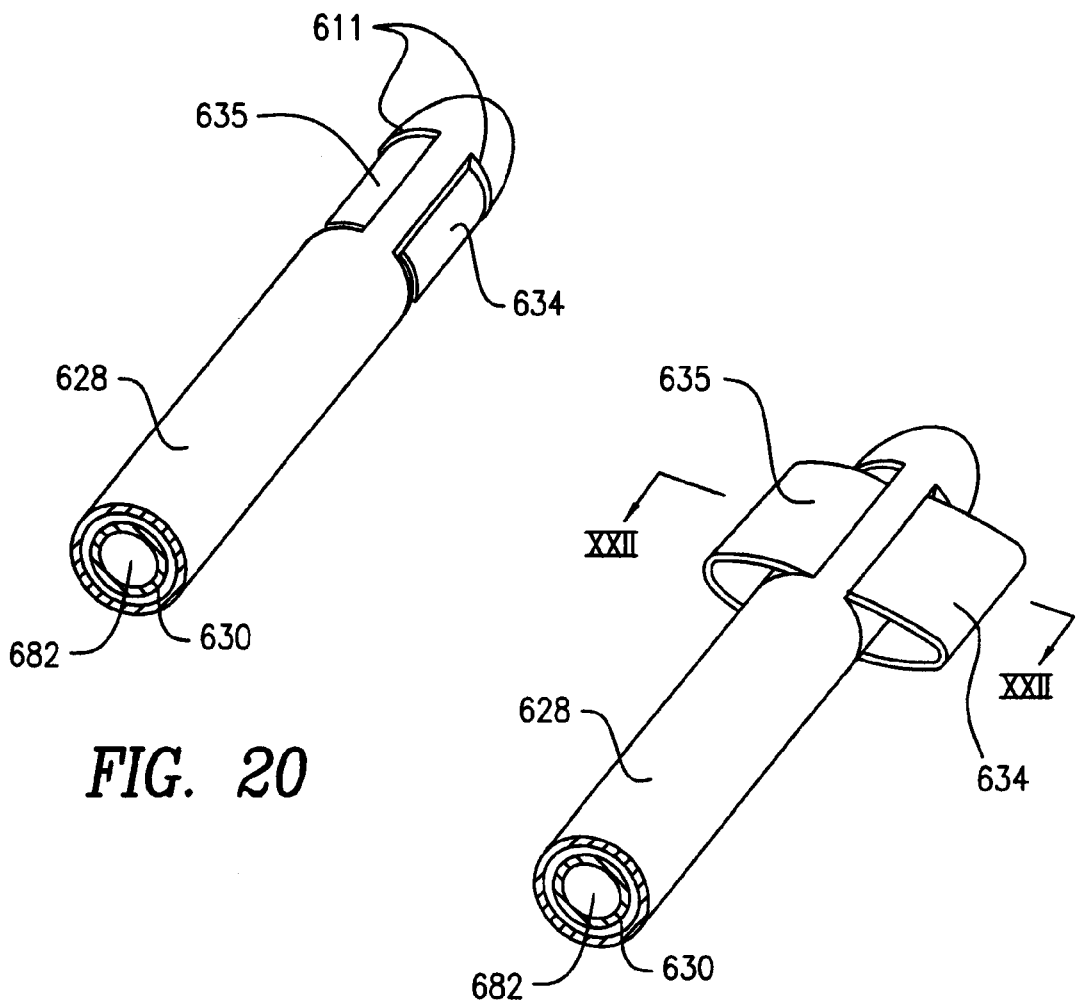
FIG. 20
FIG. 21
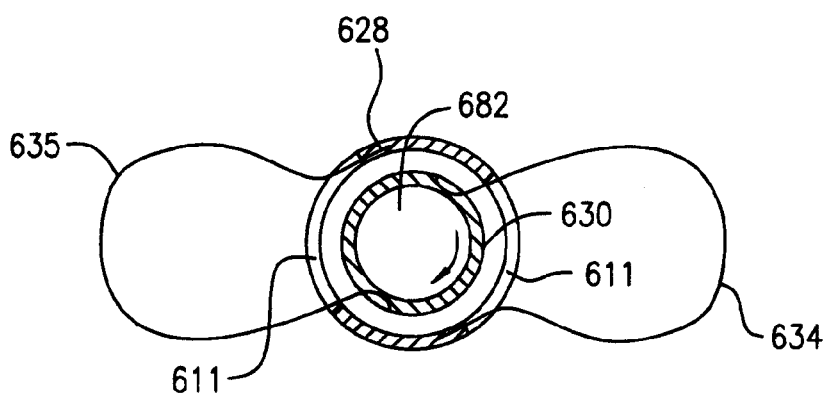
FIG. 22

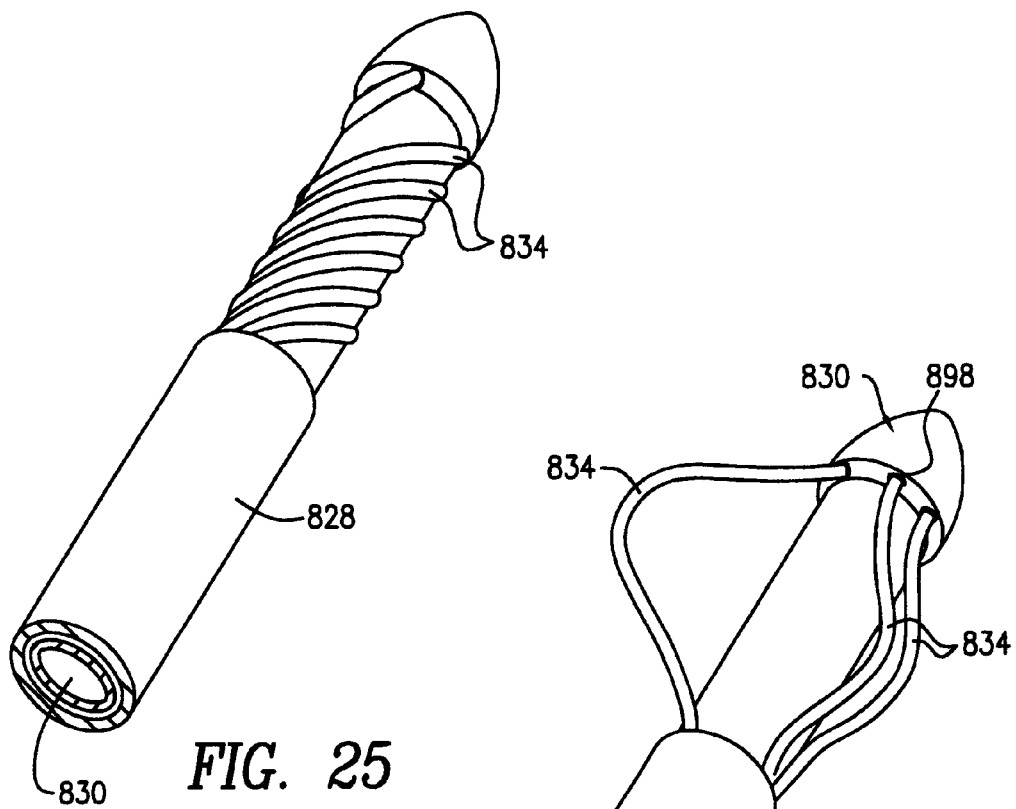
FIG. 25
FIG. 26
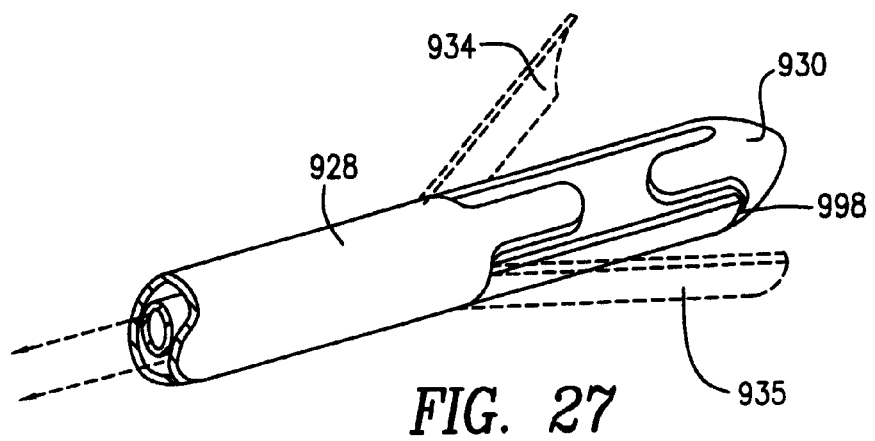
FIG. 27

SYSTEM AND METHOD FOR PLACEMENT OF A SURGICAL INSTRUMENT IN A BODY CAVITY

FIELD OF THE INVENTION

The present invention relates generally to systems and methods for optimally positioning surgical instruments within a body cavity, for example, for performing cryosurgery. More particularly, the present invention relates to a system and apparatus for filling a body cavity, such as the uterus with a fluid, e.g., thermally conductive fluid and for facilitating surgical instrument placement at an optimal position within the body cavity, e.g., the uterus, to promote an effective and efficient surgical procedure, such as cryoablation, and for permitting removal of the surgical instrument after use.

BACKGROUND OF THE INVENTION

Cryosurgery has been used for several years for the treatment and ablation of tissue for a variety of therapeutic purposes. For example, cryosurgical probes have been used for ablation of the endometrial lining of the uterus for the treatment of metrorrhagia and other disorders by freezing and killing a layer of endometrial cells. Global ablation of the endometrium is indicated to treat certain conditions wherein the entire intrauterine surface is treated in one therapy cycle. Cryoprobe placement is particularly critical in global ablation procedures in that the cryogenic effect proceeds omnidirectionally outward away from the cryoprobe tip. Accordingly, it is beneficial to optimally position the cryoprobe within the intrauterine cavity to achieve efficient global ablation. Three basic steps are required in cryoendometrial ablation, viz., (i) the introduction of a thermally conductive medium into the uterus to substantially fill the cavity for efficiently conducting heat from the endometrial lining to the cryoprobe;(ii) to place the cryoprobe within the uterus in the most effective position and activate it; and (iii) to remove the cryoprobe.

A method for necrosing endometrial cells of the uterus is disclosed in U.S. Pat. No. 3,924,628 which utilizes an expandable bladder which is inserted in a deflated condition into the uterus on the tip of a probe. After insertion into the uterus, the bladder is inflated with a gas such as nitrogen or freon which also acts as a refrigerant. As it is inflated, the bladder conforms to the interior shape of the uterine cavity. In order to conform the bladder to the shape of the uterine cavity, significant pressures are required which may be uncomfortable for the patient. The bladder also constitutes a thermal barrier to the cryogenic effect, insulating the endometrium from the nitrogen gas. Because of variations in the internal volumetric capacity of uteri within a population, it is not immediately apparent how much thermally conductive fluid is required to fill a given uterus. If fluid pressure alone is used as the indicator of a completely filled intrauterine cavity, the high pressures of distending the bladder and conforming it to the intrauterine shape reduce the relative significance of incremental pressure differences attributable to over-distending/overfilling the cavity. The bladder method therefore leads to a tendency to overfill, resulting in discomfort. As an alternative to a bladder constrained medium, the prior art has also employed unconstrained thermally conductive medium such as saline solution delivered by a catheter into the uterus.

After the thermally conductive medium has been infused into the uterus, a cryoprobe may then be placed therein. The present methods used for cryoendometrial ablation utilize ultrasound to verify the position of the cryoprobe relative to the uterus. Utilization of ultrasound adds complexity, costs and scheduling constraints to the procedure. Further, ultrasound does not guarantee that the cryoprobe will be effectively positioned in the uterus to efficiently freeze the thermally conductive medium. Actuating an improperly positioned cryoprobe fails to achieve optimal necrosing results. Accordingly, it would be beneficial to solve the problems of the prior art as set forth above.

DESCRIPTION OF THE RELATED ART

U.S. Pat. No. 5,275,595 describes a cryosurgical probe which is cooled by a refrigeration system. Cryosurgical treatment of the uterine endometrium and other tissues is described in U.S. Pat. Nos. 3,924,628, 5,647,868 and 5,520,682 and other patents. Use of particulate microcrystalline material, for example diamond suspended in a fluid carbonyl or paraffin, as a heat transfer material is described in U.S. Pat. No. 4,764,845.

U.S. Pat. Nos. 4,016,867, 4,685,474 and 4,204,548 disclose apparatus for measuring the internal dimensions of a uterus and include a caliper-type apparatus which expands to conform to the dimensions of the uterine cavity.

SUMMARY OF THE INVENTION

The limitations of the prior art methods and apparatus for performing surgery in a body cavity using a surgical instrument with a proximal portion and a probe portion are solved by the present invention which includes a positioning assembly for positioning a distal end of the probe portion within the body cavity at a selected position relative thereto. The positioning assembly has at least one positioning element which can assume a retracted position to allow insertion of the positioning assembly into the body cavity and a deployed position in which the positioning element is displaced radially outward relative to the retracted position and relative to an axis of the probe portion when the probe portion is inserted in the body cavity. The positioning element is capable of contacting an interior surface of the body cavity to move the probe portion away from the interior surface when the positioning element is deployed.

BRIEF DESCRIPTION OF THE SEVERAL VIEWS OF THE DRAWINGS

For a better understanding of the present invention, reference is made to the following detailed description of various exemplary embodiments considered in conjunction with the accompanying drawings, in which:

FIG. 20 is a fragmented perspective view of a cryoprobe tip sheath in accordance with an alternative embodiment of the present invention in the retracted position;

FIG. 21 is a fragmented perspective view of the cryoprobe tip sheath of FIG. 20 in the deployed position;

FIG. 22 is a cross-sectional view of the cryoprobe tip sheath of FIG. 21 taken along section lines XXII—XXII and looking in the direction of the arrows;

FIG. 25 is a fragmented perspective view of a cryoprobe tip sheath in accordance with an alternative embodiment of the present invention in the retracted state;

FIG. 26 is a fragmented perspective view of the cryoprobe tip sheath of FIG. 25 in the deployed state;

FIG. 27 is a fragmented perspective view of a cryoprobe tip sheath in accordance with an alternative embodiment of the present invention showing the retracted state in solid lines and the deployed state in dashed lines.

DETAILED DESCRIPTION OF THE PREFERRED EMBODIMENTS

Figure 1:
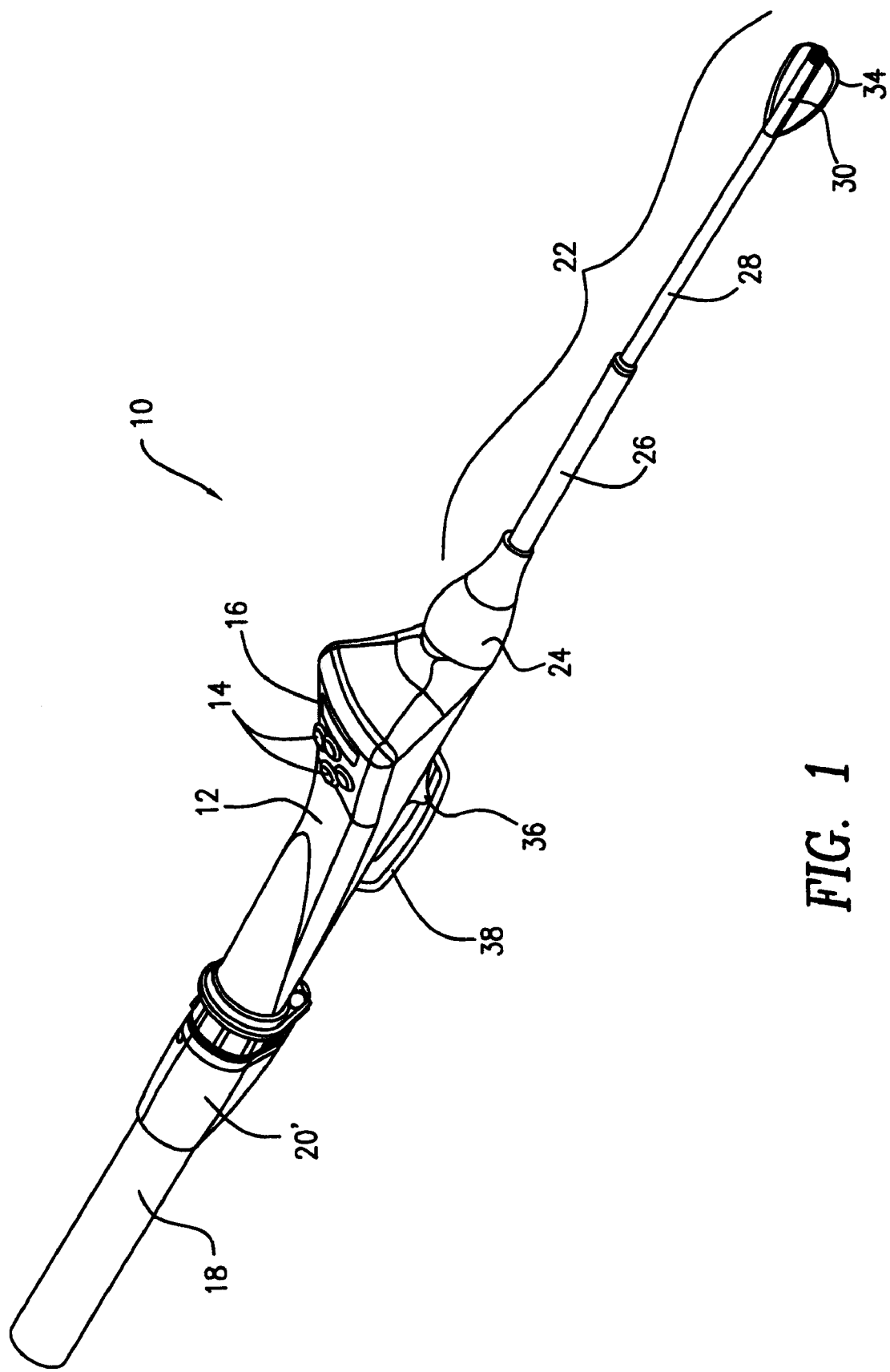
FIG. 1 is a perspective view of a cryoprobe apparatus in accordance with a first embodiment of the present invention.

FIG. 1 shows a cryoprobe assembly 10 constructed in accordance with the principles of the present invention and having a handgrip portion 12 which is gripped by the hand of the surgeon. The handgrip portion 12 has a control panel with a plurality of control buttons 14 (freeze, thaw, standby, mode) for controlling, for example, the temperature of the cryoprobe tip 86 (see FIG. 8). A visual display 16, such as an LCD display, is utilized to display the status of the centering assembly (to be described), the mode, time countdown and/or temperature of the cryoprobe tip 86. Cabling 18 is provided for connecting the cryoprobe assembly 10 to a suitable compressor or other supply of refrigerant gas via a connector 20.

A sheath assembly 22 is connected to the hand grip portion 12 by adaptor 24 which would be threaded or slotted to be removably received onto a mating extension of the hand grip portion 12. The sheath assembly 22 is received over the cryoprobe tip 86 (FIG. 8) for the purpose of shielding the cryoprobe tip 86 from potential contamination by bacteria or viruses that may be present in the uterus of the patient in which it is used. After use, the sheath assembly may be disconnected from the remainder of the cryoprobe 10 for separate sterilization, e.g., in an autoclave, sterilizing solution and/or irradiation. Alternatively, the sheath assembly 22 may be disposed of after a single use thereby avoiding the expensive and possibly ineffective process of sterilization. Depending upon the cost of the hand grip portion 12, it may be preferable to dispose of it after each use if disposal is more cost effective than sterilization. The sheath assembly 22 includes an intermediate shaft 26 into which telescopes an actuator tube 28. The intermediate shaft 26 may be of greater diameter because it is not introduced into the uterus. The intermediate shaft 26 may house actuating or urging mechanisms for moving the actuator tube 28, as will be described below. The actuator tube 28 is coaxially received over a probe sheath 30, the distal portion of which is visible in FIG. 1. The probe sheath 30 is preferably formed from heat conductive material such as stainless steel, is the stationary central portion of the assembly 22, and covers the cryoprobe tip 86, diminishing the need for extensive sterilization of the cryoprobe 10. A pair of positioning elements 34, 35 extend from the distal end of actuator tube 28 and are shown in a deployed position. The deployment of the positioning elements 34, 35 may be controlled by an actuator trigger/lever 36 guarded by shield 38.

The use and structure of a probe sheath 30 is disclosed and described in application Ser. No. 09/087,113 filed May 28, 1998 entitled "Cryosurgical System and Method" owned by the assignee herein and which is incorporated herein by reference for its teachings concerning the construction and operation of cryoprobes and cryoprobe sheaths, e.g., to avoid cross-contamination. The present invention contemplates a variety of options with respect to disposability of elements ranging from sterilization and reuse of the entirety of the instrument to disposal of the entirety after a single use. Because surgical use gives rise to a probability that the patient's bodily fluids will be transferred to the intermediate shaft 26 and adapter 24, they may be disposable. Depending upon technique, the surgeon's hands may contact the patient's bodily fluids and then subsequently contact the remainder of the cryoprobe assembly 10, e.g., when gripping the handgrip portion 12 or pressing the control buttons 14, such that the entire probe 10 must either be sterilized or disposed of.

Figure 2:
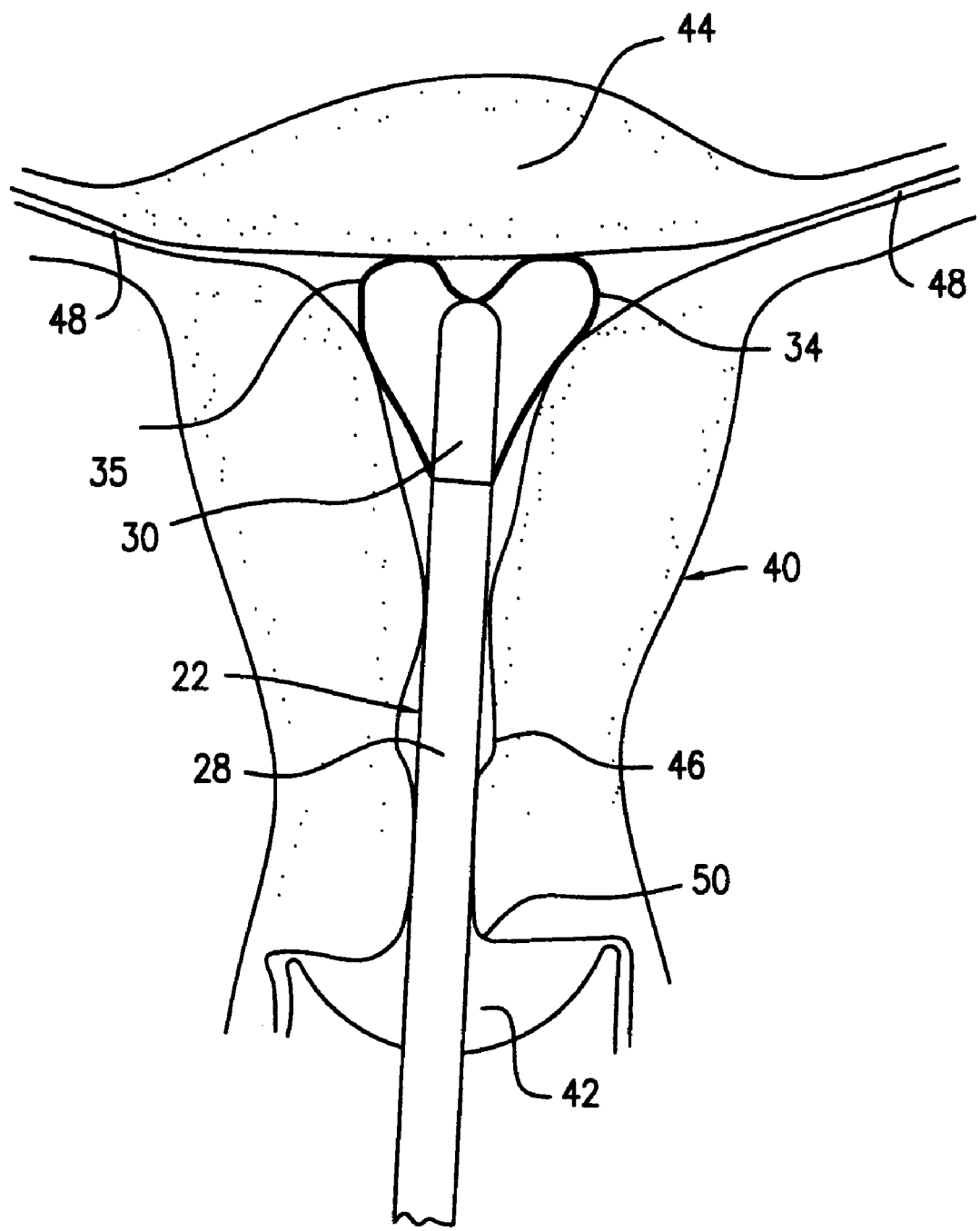
FIG. 2 is a diagrammatic cross-sectional view of a uterus with the tip of the cryoprobe shown in FIG. 1 in place within the uterus.

FIG. 2 shows the distal end of the sheath assembly 22 placed within a uterus 40 with the actuator tube 28 pushed forward to deploy the positioning elements 34 and 35. As can be appreciated, the sheath assembly 22 extends through the cervix 42 at the cervical os 50, through the isthmus of the uterine cavity 46 with the tip of the sheath 30 proximate to the fundus 44. Upon deployment, the positioning elements 34 and 35 of the embodiment shown in FIG. 2 displace the distal end of the probe sheath 30 laterally within the uterine cavity such that it is approximately centered with respect to the fallopian tubes 48. Alternatively, the positioning elements 34, 35 can be configured to position the probe sheath to one side or the other of the uterus. Substantially symmetrical positioning elements 34, 35 are especially appropriate for a single probe placement and freeze/thaw cycle. Asymmetric positioning elements 34, 35 may be utilized in multiple stage procedures wherein the cryoprobe is positioned at a first position within the uterus and a first freeze/thaw cycle initiated followed by repositioning the cryoprobe to a second position within the uterus followed by the initiation of a second freeze/thaw cycle. Multiple freeze/thaw cycles may be initiated as required for the specific procedure undertaken.

The positioning elements 34, 35 deploy within a common or parallel plane that is perpendicular with respect to the orientation of the control buttons 14 and display 16 such that the surgeon may orient the positioning elements 34, 35 relative to the uterus based upon the orientation of the hand grip portion 12 relative to the general orientation of the patient's body. In addition to their lateral positioning function, the positioning elements 34 and 35 displace the distal tip of the sheath 30 away from the wall of the fundus, thus cushioning the tip of the sheath 30 and preventing the tip from penetrating the fundus 44. The positioning elements 34, 35 may be formed from stainless steel, nitinol tubing, thermoplastics, or wire and may be coated with materials such as a polymer/plastic coating to decrease frictional interaction with a thermally conductive medium.

Figure 3:
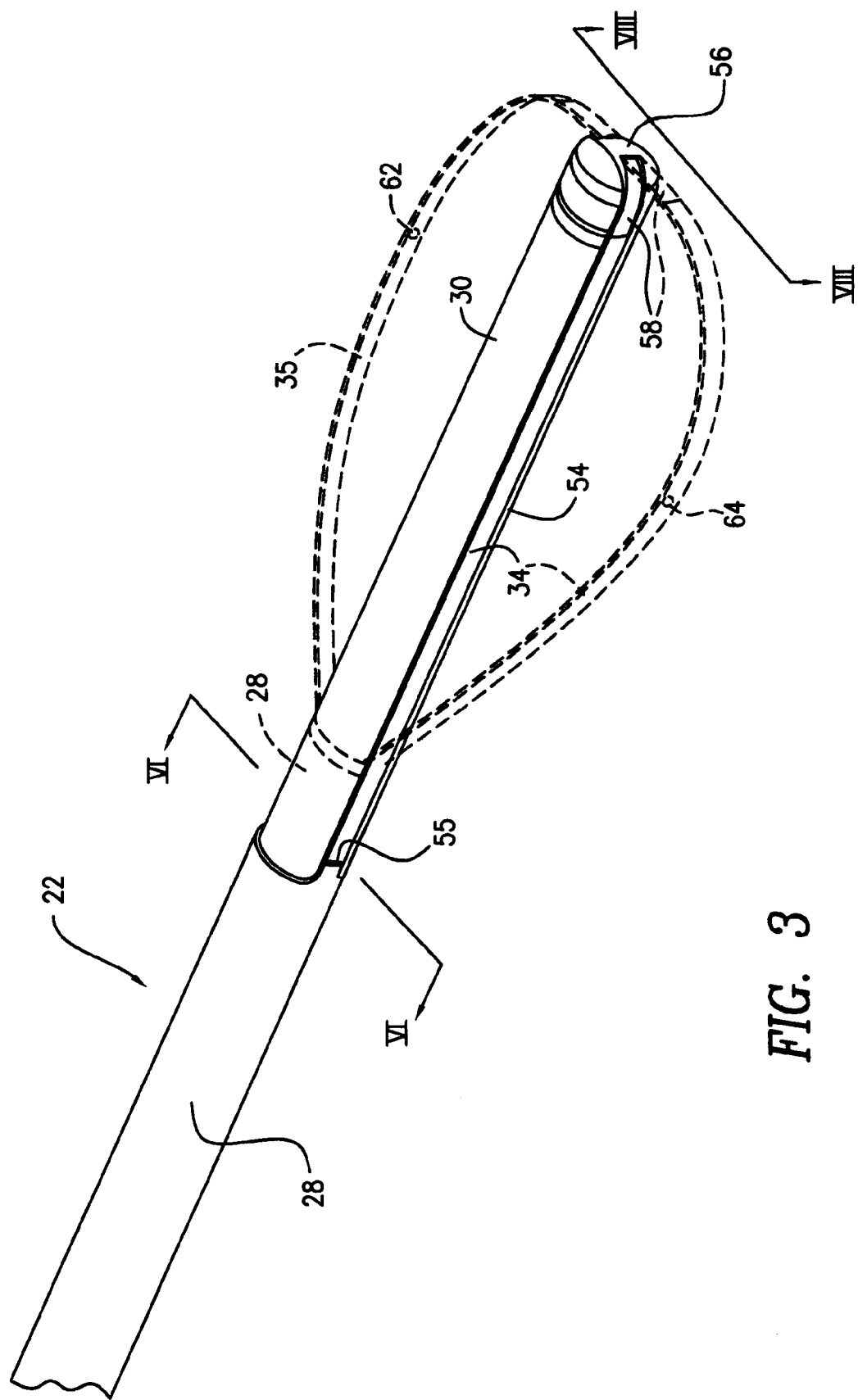
FIG. 3 is an enlarged view of the tip of the cryoprobe of FIG. 1 showing the retracted position of a positioning apparatus in solid lines and the deployed position in dotted lines.
Figure 4:
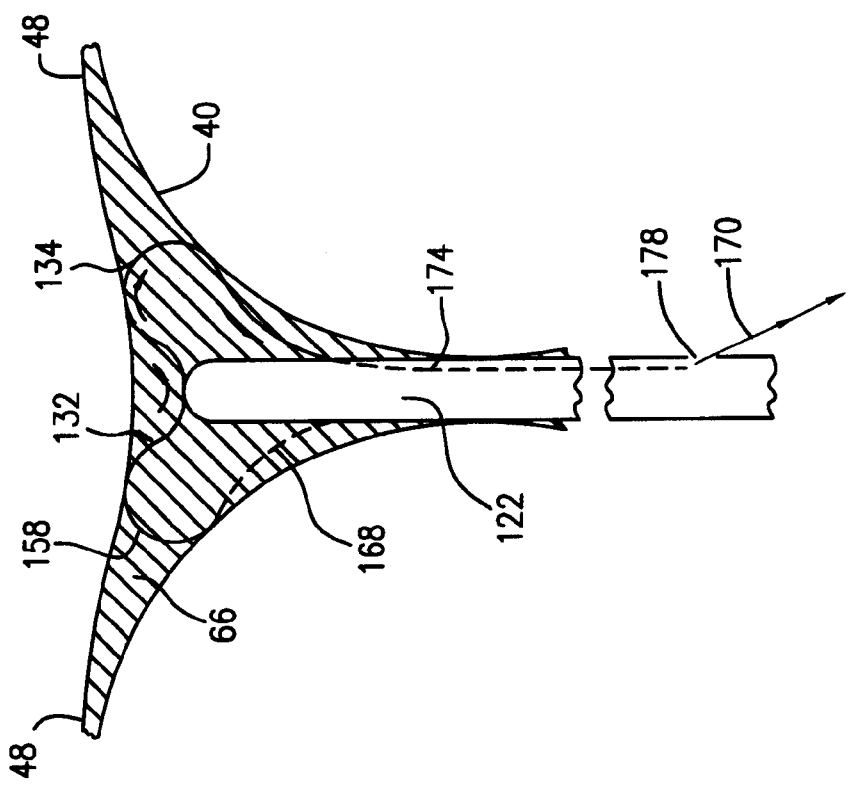

FIG. 3 shows an enlarged view of the distal end of the sheath assembly 22 in its retracted (solid lines) and deployed states (dotted lines). In the retracted position, the positioning elements 34 and 35 are received within channels 54 such that when in the retracted position, the exterior surface is smooth and inserts smoothly through the cervical os. As can be seen in FIG. 3, the positioning elements 34 and 35 are contiguous with the actuator shaft tube 28 which telescopes over the probe sheath 30. In order for the positioning elements 34 and 35 to have their outer surface at the same level as the outer surface of the probe sheath 30 and be received within the channels 54, there is a traversal from the diameter of the actuator tube 28 to the level of the channel 54 at transition line 55 where an inward bending occurs. In the embodiment shown in FIG. 3, the positioning elements 34 and 35 both have a free end 58 which extends beyond a pivot 56 and wraps around the tip of the probe sheath 30 in the retracted position. In this embodiment, one free end 58 overlaps another such that when the positioning elements are deployed, one free end 58 will override the underlying positioning element 34. The other free end, which is not visible in this view, will retain its position overlapping the tip of the probe sheath 30. The positioning elements 34, 35 are free at the ends in order to allow them to be withdrawn from solidified thermally conductive media as can be seen in FIG. 4. Thermocouples 62 and 64 may be provided in the positioning elements 34 and 35 in order to obtain a temperature reading at that point. Temperature readings taken on complementary sides of the uterus can indicate whether an even cooling is taking place. In the eventuality that nitinol tubing is used for forming the shims 34, 35, thermocouples can be threaded through the lumen of the tubing to check the temperature at selected points along the length of each shim 34, 35.

Figure 5:
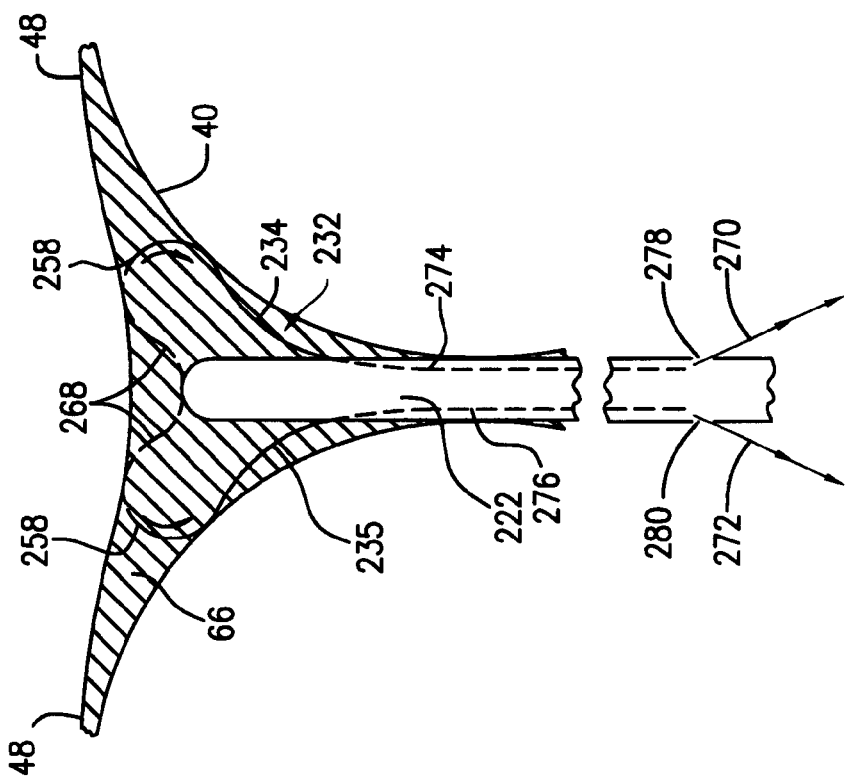
FIGS. 4 and 5 are diagrammatic views of the withdrawal of positioning elements from a uterus having a thermally conductive material therein.

FIGS. 4 and 5 diagrammatically depict a uterus 40 which has been filled with a thermally conductive medium 66 such as a sterile jelly, water or saline solution. Viscous media 66 such as medical grade jellies, e.g., KY Jelly, silicone jellies, and low freezing point hydrogels are preferred for cryoablation. A cryoprobe sheath assembly 122 has been inserted and the positioning assembly 132 actuated. In FIG. 4, the positioning assembly 132 is in the form of a continuous shim or wire 134 which is removably attached to the sheath assembly 122 at one free end 158 and has a withdrawn end 170 which is gripped by a withdrawing mechanism or the hand of the surgeon, allowing the shim 134 to be pulled through its track 168 in the thermally conductive media after it has been frozen. The shim 134 passes through a lumen 174 provided in the sheath assembly 122 and out an exit port 178. When the positioning assembly 132 has been withdrawn, the sheath assembly 122 may then be withdrawn from the uterus 40.

The process for using the present invention therefore includes: (1) filling the uterus with a heat conductive medium 66; (2) inserting the sheath assembly 122 (and underlying cryoprobe 86); and (3) deploying the positioning apparatus 132 to position the tip of the distal end of the sheath assembly 122 in a suitable position within the uterus. For global ablation, the sheath assembly 122 is preferably centered between the fallopian tubes 48 to allow for even cooling of medium 66 and an even cryogenic effect upon the endometrial lining of the uterus 40. After the sheath assembly 122 has been positioned by positioning assembly 132, the cryogenic probe 10 is actuated, freezing the thermally conductive medium 66 thereby freezing the endometrial lining. While the medium 66 is chilled and/or frozen, the positioning element 134 can be withdrawn through its own track 168 in the frozen media 66 and then through a lumen 174 provided in the sheath assembly 122, and out an outlet port 178. The sheath assembly 122 may then be withdrawn from the frozen medium 66 to allow the removal of the cryoprobe 10 from the uterus.

A similar procedure is diagrammatically illustrated in FIG. 5 wherein the positioning assembly 232 includes a pair of positioning elements 234 and 235 each of which has a free end 258 such that their simultaneous withdrawal by exerting a force at their withdrawing ends 270 and 272 causes the positioning elements 234, 235 to pull through their corresponding track 268 after the heat conductive medium 66 is chilled and/or frozen. It should be appreciated that the embodiments of the present invention shown in FIGS. 4 and 5 differ from that which is shown in FIG. 3 in that a lumen 174, 274, 276 is provided in the sheath assembly 122, 222 for slidably receiving a corresponding positioning element 134, 234, 235 to permit the positioning element to be deployed and withdrawn. In FIG. 3, a lumen is not provided, but a channel 54 receives the positioning elements 34, 35 and deploying and retraction is accomplished by the actuator tube 28.

It can be appreciated from the foregoing that the present invention provides a method and apparatus for positioning a cryoprobe in the uterus with mechanical means and without the use of an ultrasound, fluoroscope or any other external equipment. The present invention also permits the positioning device to be removed after the cryoprobe has been positioned. This can be done either before the freezing cycle starts or after freezing has been completed. While FIGS. 4 and 5 have been described as illustrating the removal of the positioning elements 134, 234, 235 from the medium 66 after it has been solidified by the cryogenic probe, the positioning elements can be withdrawn from the medium 66 prior to completely solidifying it or it can be withdrawn after a thaw cycle. The positioning assembly 132 can be used to position the probe in the correct position and the cryoprobe 10 activated momentarily to freeze or tack the distal end of the sheath assembly 22 in the desired position. The positioning assembly can then be withdrawn prior to completing the cryogenic cycle to solidify the entire medium 66 filling the uterine cavity. Accordingly, the present invention can be utilized by inserting the probe, deploying the positioning assembly 132 and then tacking the probe with a momentary actuation followed by withdrawal of the positioning assembly 132. As shown in FIGS. 4 and 5, the centering assembly 132 can also be removed from the uterus after the freezing cycle has been completed and the heat conductive medium 66 solidified. As can be appreciated from the foregoing, the present invention provides lateral centering but also can provide spacing of the distal end of the sheath assembly 22 from the fundus, both for the purpose for positioning the probe longitudinally and to provide a cushioning effect to prevent the uterus from being penetrated or injured by the cryogenic probe 10.

Figure 6:
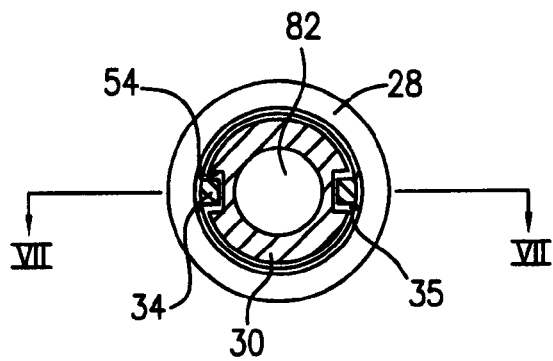
FIG. 6 is a cross-sectional view of the cryoprobe tip of FIG. 3 taken along section line VI—VI and looking in the direction of the arrows.
Figure 7:
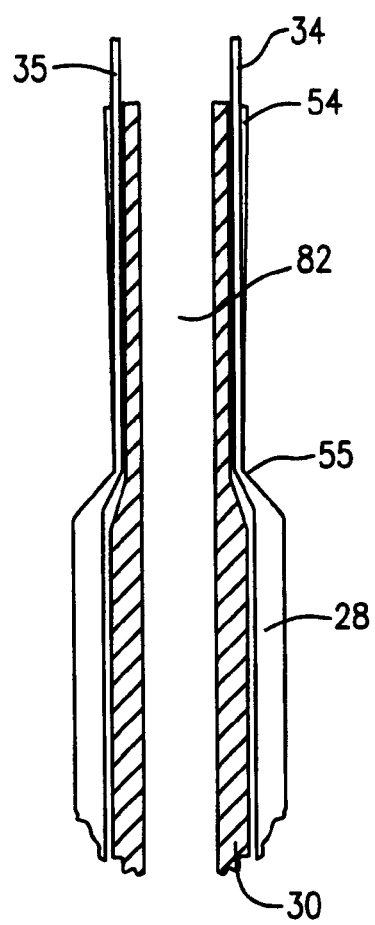
FIG. 7 is a cross-sectional view of the cryoprobe shown in FIG. 6 taken along section line VII—VII and looking in the direction of the arrows.

FIGS. 6 and 7 show further structural details of the embodiment of the present invention depicted in FIG. 3. As noted above, the positioning elements 34 and 35 extend from the actuator tube 28 and at transition point 55 extend into channels 54 such that they do not extend above the surface of the probe sheath 30 in the area where it is inserted through the cervical os. The actuator tube 28 is preferably manufactured to close tolerances relative to the sheath 30 such that it can readily be slid through the cervical os without significant radial displacement of the cervix. The tip of the tube 28 can be tapered inwardly to further facilitate a gentle introduction of the tube 28 through the cervical os. As can be appreciated from FIGS. 6 and 7, the sheath 30 has a cryoprobe lumen 82 extending through the center thereof for admitting a cryoprobe tip 86. The dimensions selected for these figures are used for illustration purposes only, in that the optimum dimensions, e.g., the wall thickness of sheath 30, are minimal to maximize heat transfer and to minimize the diameter of the sheath assembly 22 that is introduced into the uterus.

Figure 8:
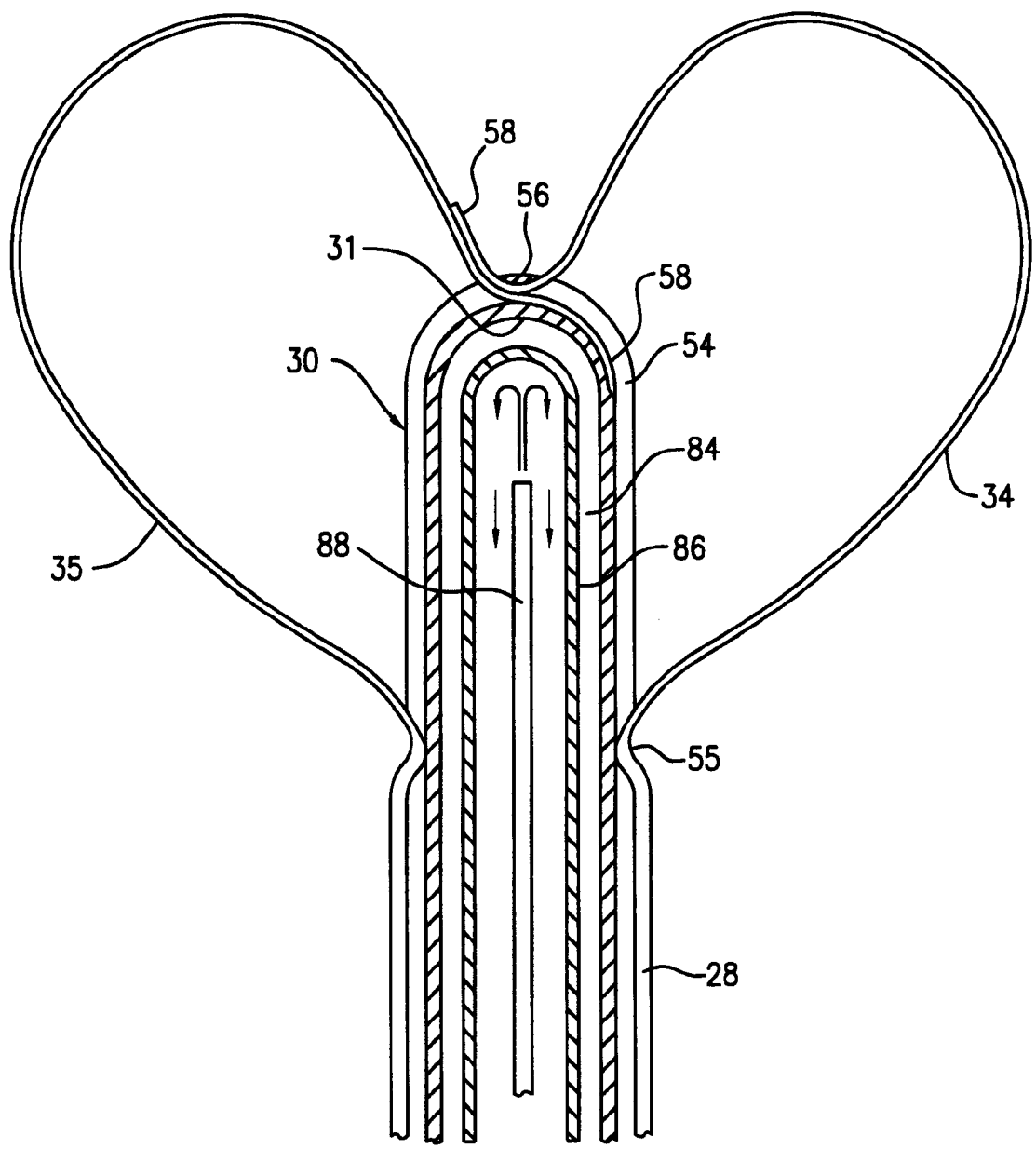
FIG. 8 is a cross-sectional view of the cryoprobe tip shown in FIG. 3 taken along section lines VIII—VIII and looking in the direction of the arrows.
Figure 15:
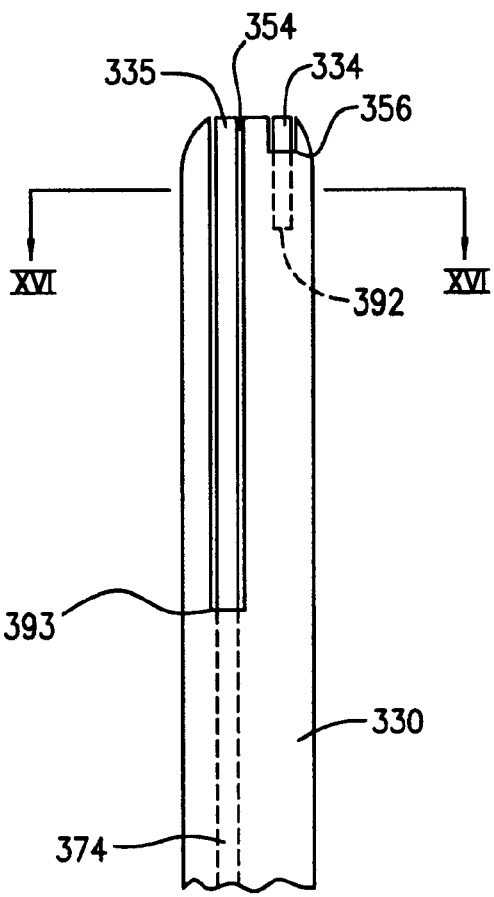
FIG. 15 is an enlarged view of a cryoprobe tip sheath and positioning elements in accordance with an alternative embodiment of the present invention.

FIG. 8 illustrates how the probe sheath 30 with blind distal end 31 and lumen 84 coaxially covers the cryoprobe tip 86 with a peripheral space therebetween filled with a heat conductive paste as described in application Ser. No. 09/087, 113 which has been incorporated herein by reference. The cryoprobe tip 86 is cooled using known principles and apparatus, for example as referred to in application Ser. No. 09/087,113, and typically incorporates a refrigerant discharge tube 88 proximate to the distal end of the cryoprobe tip 86 such that when refrigerant in a liquefied or semi-liquid state exits the refrigerant discharge tube 88 and converts to a gas, the heat of vaporization is absorbed from the cryoprobe tip 86 and its surrounding environment. The expanded refrigerant gas is then conducted back to its origins or is vented to the atmosphere, depending upon the particular cryoprobe technology employed. FIG. 8 illustrates in cross-section how the positioning elements 34 and 35 extend from the actuator tube 28 and descend from the outer periphery of the sheath 30 into the channel 54 at the transition point 55. The overlapping free ends 58 of the positioning elements 34 and 35 can be seen positioned against a pivot 56 provided at the distal end of the probe shield 30. The probe shield 30 may have a channel or groove carved therein to accommodate the free end 58 which contacts it, i.e., the free end 58 associated with positioning element 35. The other free end 58 of positioning element 34 overlaps positioning element 35 and is displaced upward when the positioning elements are deployed by the actuator tube 28. The positioning elements 34, 35 may have a variable width, e.g., with the portions proximate free ends 58 being narrower than the portion which contacts the uterus, In this respect, it is beneficial for the positioning elements to be wider at their contact surfaces because the broader the area of contact, the less force per unit area is exerted on the uterus by the positioning elements upon deployment. While FIG. 8 illustrates an embodiment wherein the positioning elements 34, 35 overlap, they can also be laterally offset as shown in FIG. 15, to be described below.

Figure 9:
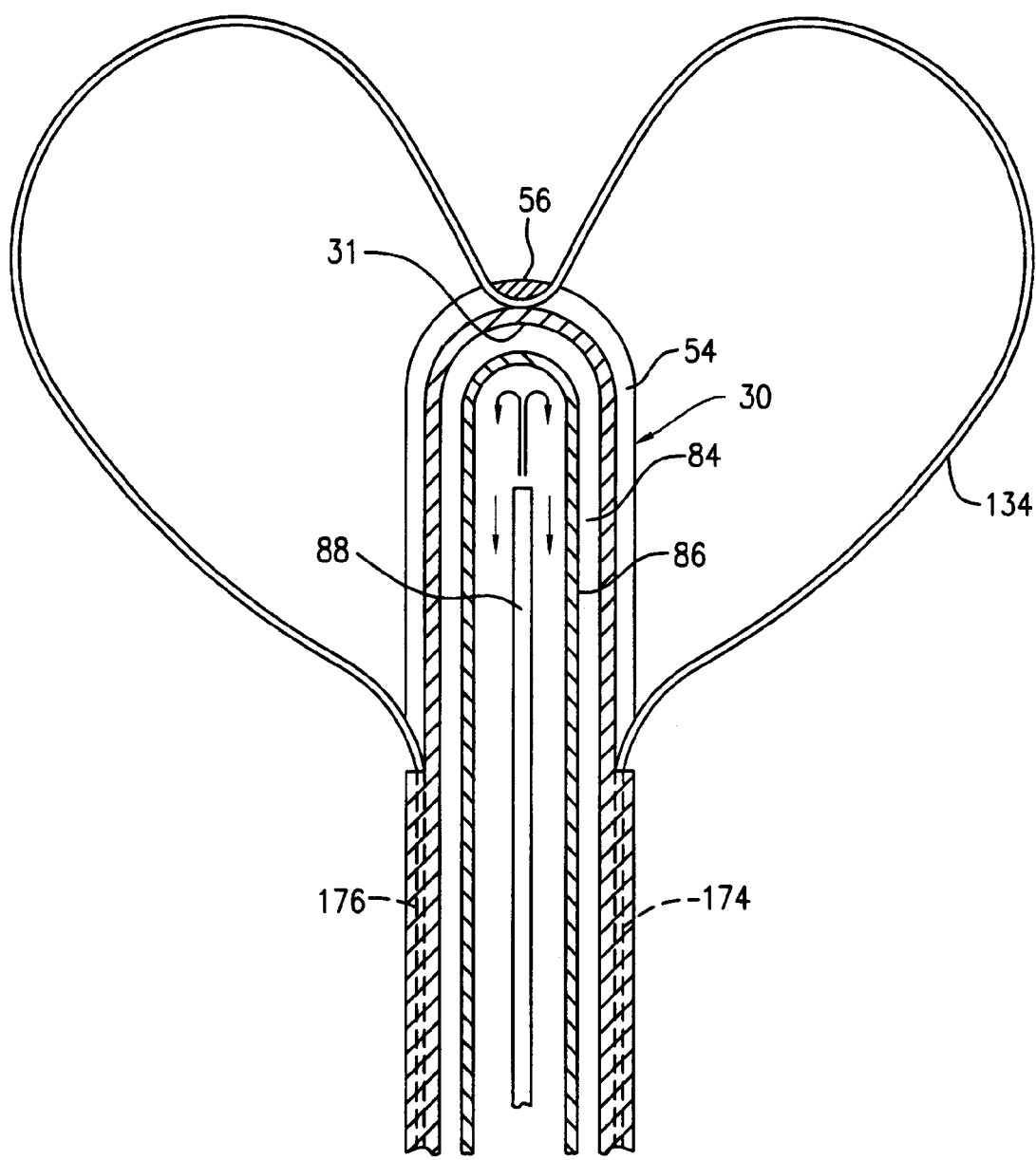
FIG. 9 is a cross-sectional view like FIG. 8 of an alternative embodiment of the present invention.

FIG. 9 depicts an alternative embodiment in which a pair of lumens 174 and 176 slidingly accommodate a continuous positioning element 134 which passes therethrough down to the base of the cryoprobe sheath where an actuator mechanism deploys and retracts it. In this embodiment, one of the ends of the continuous positioning element 134 needs to be removably inserted in a receiver. When the other end of the positioning element 134 is pulled to withdraw it from the intrauterine space, the free end can travel through its associated lumen and the heat conductive medium in order to be withdrawn from the deployed position, as shown in FIG. 4. Alternatively, the continuous positioning element 134 may be frangible at a point along its length.

Four different strategies for positioning element deployment and use are shown in FIGS. 10–13. In each of FIGS. 10,11,12 and 13, the positioning assembly 132, 232, 332, 432 includes an actuator portion 96, a transition portion 94 and a positioning element portion 191, 291, 391, 491. The positioning element portions diverge from the transition portion 94 at a divergence point 93. That is, the divergence point 93 is where the positioning elements, e.g., 234, 235 diverge from their generally parallel retracted position to their laterally expanded deployed position. With reference to the embodiment shown in FIG. 8, the transition portion 94 is equivalent to the actuator tube 28. The divergence point 93 in the embodiment shown in FIG. 8 is approximately at the transition line 55. In the embodiment shown in FIG. 9, the transition region 94 includes the lumens 174 and 176 and the divergence points 93 occur at the distal openings of the lumens 174 and 176 as they enter the channels 154. In both FIGS. 8 and 9, the actuator mechanism 96 is not shown.

Figure 10:
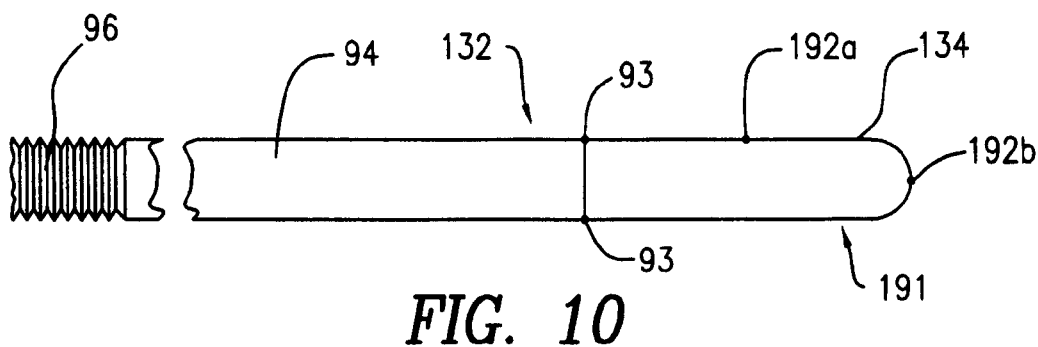
FIGS. 10–13 are diagrammatic views of four alternative embodiments of positioning assemblies in accordance with the present invention.

As noted above, the positioning mechanism of the present invention may utilize a positioning element pivot 56 which urges the positioning assembly 132 into its cardioid shape when deployed. In order to be withdrawn from the uterus after having accomplished the positioning function, the positioning elements, e.g., 34, 35, must have a free end or ends such that they may be withdrawn through the thermally conductive medium if it is solidified. In FIG. 10, the free end is provided by a frangible point 192a or 192b in an otherwise continuous positioning element 134. The frangible point may also exist at the divergence point 93 or may reside in the transition portion 94. In any case, when the actuator mechanism 96 is actuated in the direction of retraction, the forces conducted through the transition portion 94 to the positioning element portion 191 cause the frangible point 192a and 192b to break and allow the positioning element 134 to travel in opposite directions, as shown in FIG. 5, to be withdrawn from the uterus. As an alternative to breaking, one end of the positioning elements 134 may be tucked into a suitable slot provided in the transition portion 94.

Figure 11:
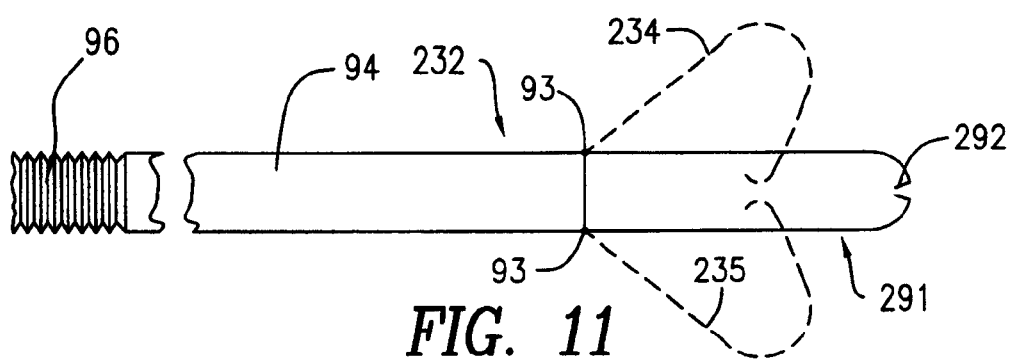

FIG. 11 illustrates an embodiment of the present invention utilizing a pair of positioning elements 234, 235 that have a preset cardioid shape when in the relaxed state. Each of the prestressed, preshaped positioning elements 234, 235 is attached to the transition portion 94 and diverge from the sheath 30 when the transition portion 94 travels towards the tip of the sheath 30 (see FIG. 1). In FIG. 11, the positioning elements 234, 235 are shown in their retracted state in solid lines and in the deployed state in dotted lines. Each of the prestressed positioning elements 234, 235 has a free end 292 which would be received in a suitable recess provided at the tip of the probe sheath 30 (not shown).

Figure 12:
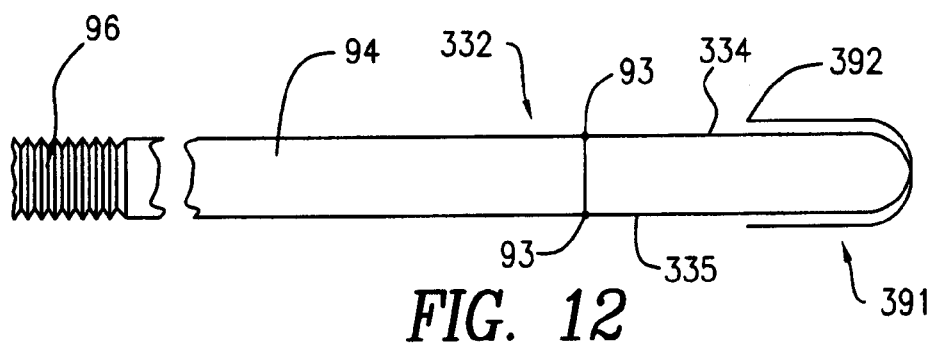

FIG. 12 shows an embodiment of the present invention wherein the positioning elements 334, 335 have ends 392 which overlap the tip of the probe sheath 30. The degree of overlap can be similar to FIG. 3 or greater as shown in the embodiment of FIG. 15 which will be further described below in reference to that figure.

Figure 13:
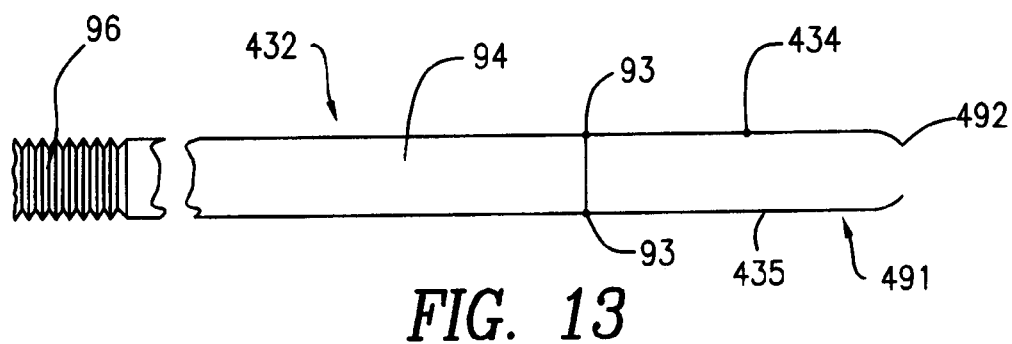

FIG. 13 diagrammatically shows an embodiment of the present invention utilizing a pair of positioning elements 434, 435 which terminate at free ends 492 which do not extend beyond the tip of the probe sheath 30 but rather insert into suitable recesses along the length of the sheath 30 proximate the distal end thereof. This embodiment is further described and illustrated in FIGS. 23–27 below. The positioning elements 434, 435 may either be straight in their relaxed state and urged into a cardioid shape or may be prestressed to assume a relaxed shape that facilitates positioning the cryoprobe 10.

Figure 14:
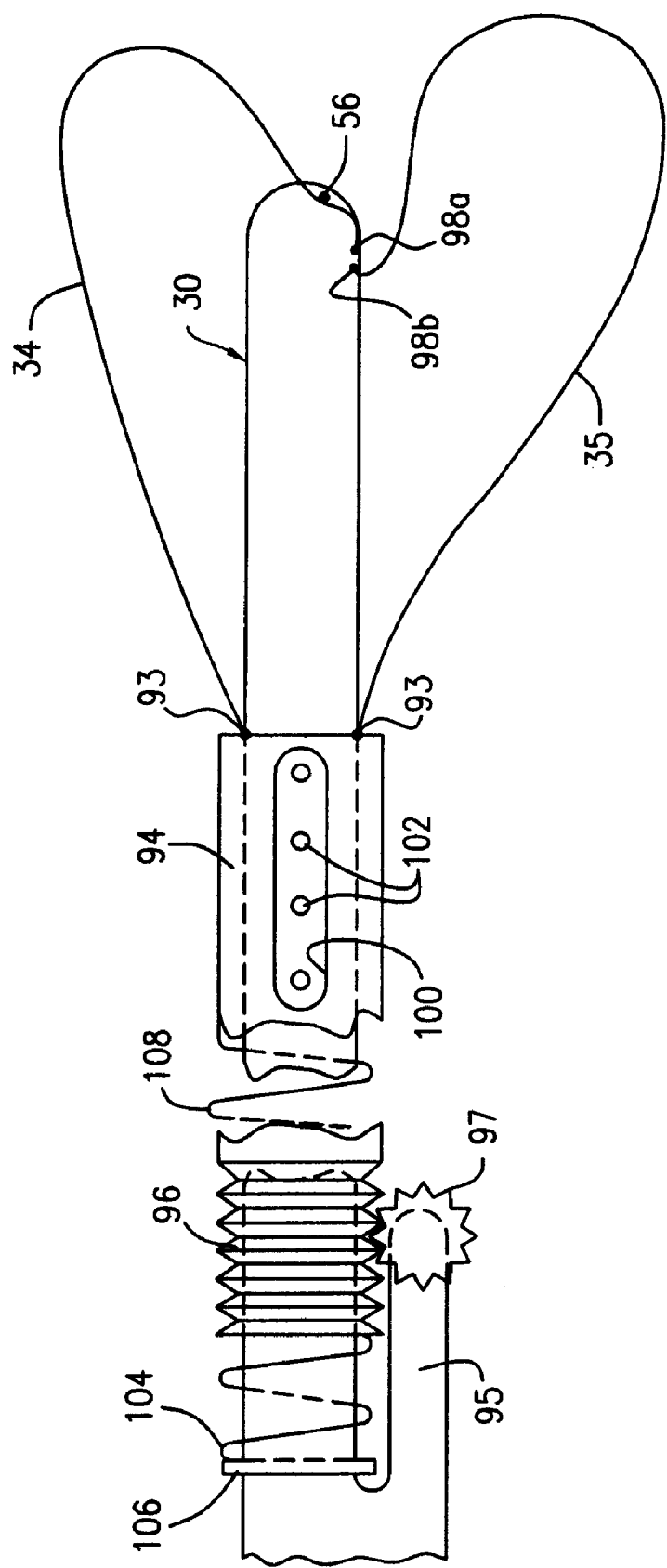
FIG. 14 is an enlarged view of a cryoprobe positioning assembly in accordance with an alternative embodiment of the present invention.

FIG. 14 illustrates diagrammatically some additional features that may be incorporated into the present invention. In general, it is noted that the positioning assembly 32 has certain movable parts that move relative to a stationary element or base member, namely the probe sheath 30. The positioning elements 34, 35 are deployed and retracted via the action of an actuator mechanism 96 acting upon a transition portion 94 which urges the positioning elements 34, 35 into a cardioid shape beginning at the point of divergence 93. The actuator 96 may be any known mechanical actuation mechanism for sliding one element relative to another. In the embodiment shown, the actuator mechanism 96 is a toothed collar which rides over the probe sheath 30 or a basal element in structural continuity with the probe sheath 30. As the actuator 96 has teeth, it may be used to interact with another toothed member such as a gear wheel 97 rotatably attached to extension 95 and driven by a ratchet and trigger 36 (FIG. 1) that the operator of the device may employ to deploy and retract the positioning elements 34 and 35. Alternatively, a hand-wheel or hand-crank can turn the gear wheel 97 or a simple thumb slide may be provided to allow the surgeon to move actuator element 96 toward the distal end of the probe sheath 30. While a cylindrical actuator collar 96 is depicted, the actuator 96 could be an elongated toothed member (rack) sliding within a track provided in the probe sheath 30 or other structural support for the sheath 30. As noted above, the transition portion 94 of the positioning assembly 32 may be in the form of a tubular member which is structurally integrated with the actuator 96 at one end and with the positioning elements 34 and 35 at the other end. As further noted above, the transition portion 94 may also be integral with the sheath or rigidly affixed to the sheath in the form of a pair of lumens extending therethrough to accommodate the positioning elements 34, 35 from the divergence point 93 back to the actuator element 96.

In FIG. 14, the positioning elements 34 and 35 are of two different types for the purposes of showing the different possibilities for constructing and using the positioning assembly 32. Positioning element 34 passes behind pivot 56 to end retention point 98a. Positioning element 35 shows an alternative form of end placement and retention in that the free end of the positioning element is retained in a receptacle 98b positioned further from the tip and without utilizing a pivot 56. The deployed shape of the positioning elements 34 and 35 depend on several factors including the relaxed shape of the positioning element, the torsional rigidity of the positioning element along various points of its length, the presence/location of a pivot and the location of the end retention point 98. In addition to the resultant deployed shape of the positioning elements 34 and 35, as defined by the various mechanical and dimensional attributes of the positioning elements and their interaction with the sheath assembly, the deployed shape will also be effected by its interaction with the uterus.

FIG. 14 depicts an embodiment wherein the positioning elements 34 and 35 are asymmetric. This condition can be utilized to perform a two step ablation procedure wherein the asymmetric positioning elements 34, 35 position a cryoprobe off-center in the uterus. The cryoprobe is then activated, freezing the thermal conductive medium on the side of the uterus in which the cryoprobe has been positioned. The cryoprobe is then removed from its first position, the positioning elements reoriented in the opposite direction and redeployed to position the cryoprobe on the opposite side of the uterus which then is treated by actuating the cryoprobe. As an alternative to asymmetric positioning elements, the positioning elements 34, 35 may be independently deployable such that a two step ablation with repositioning may be accomplished by actuating a first positioning element to displace the cryoprobe in a first direction followed by actuation. A second step follows removal of the cryoprobe from its first position, deployment of the second positioning element and a subsequent actuation of the cryoprobe to freeze the second side. In addition to positioning and freezing, a thaw cycle can be included in the procedure at each sequential positioning.

In general, it is desirable to exert the minimum force for centering, insertion and/or otherwise maneuvering the cryoprobe 10 and the positioning assembly 32 within the uterus to avoid trauma to the uterus. Accordingly, the positioning element tension should be selected such that it can position the probe 10 without placing undue forces on the uterus. FIG. 14 illustrates three additional features that may be incorporated into the present invention to minimize the risk of subjecting the uterus to unnecessary trauma. Due to the fact that uteri vary in dimensions based upon the individual and their age, genetic makeup, etc., the centering apparatus will need to be deployed to a greater or lesser extent for larger or smaller intrauterine cavities, respectively. As is known in the art, intrauterine dimensions may be measured by intrauterine caliper and sound devices. Upon ascertaining the intrauterine dimensions for a particular patient, the degree of deployment of the positioning device of the present invention can be tailored to the particular patient and her specific intrauterine dimensions by means of an adjustable deployment stop/control mechanism which can operate on the transition portion 94 and/or the actuator mechanism 96, 97. FIG. 14 illustrates a deployment travel limiter slot 100 provided in the transition portion 94 and a plurality of stop buttons or pins 102 which may be raised or lowered to engage the edge of the slot 100 in order to limit the motion of the transition portion 94 and thereby the deployment travel of the transition portion 94. Alternatively, an adjustable travel stop could act against actuator elements 96, 97, 98.

As yet another safety mechanism, a force limiting spring 108 may be introduced between the actuator 96 and the transition portion 94. The force limiting spring 108 can be used to absorb the deployment travel attributable to the actuator 96 in the eventuality that positioning elements 34, 35 encounter intrauterine resistance to deployment. In this manner, the spring 108 absorbs the force that would otherwise be exerted on the positioning elements 34, 35, for example when centering the probe in a uterus that has smaller internal dimensions than the average.

As yet another feature to avoid placing excessive forces on the positioning elements 34, 35 and the uterus, a deployment spring 104 may be utilized to supply the urging force propelling the actuator 96 forward, resulting in the deployment of the positioning elements 34, 35. In an embodiment utilizing the deployment spring 104, the actuator gearing or linkage, for example 96, 97, would be used as a brake which is released to permit the deployment spring 104 to actuate the deployment of the positioning elements 34, 35. The actuating mechanisms 96, 97 can then be used to retract the positioning elements against the force of the deploying spring 104. By utilizing the deployment spring 104, the force exerted on the positioning elements 34, 35 is limited to that which is inherent in the resilience of the spring 104.

Figure 16:
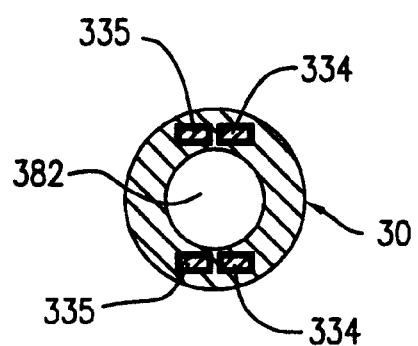
FIG. 16 is a cross-sectional view of the cryoprobe tip sheath of FIG. 15 taken along cross-section lines XVI—XVI and looking in the direction of the arrows.

FIGS. 15 and 16 depict an embodiment of the present invention having offset overlapping positioning elements 335, 334. As can be appreciated from FIG. 15, the transition portion constitutes a lumen 374 through a probe sheath 330 which terminates in a recessed channel 354 that extends up and over the distal end of the probe sheath 330. The channel 354 continues over to the other side of the probe sheath 330 to accommodate a free end of each positioning element 392. As a consequence, a diversion point 393 is the opening of the lumen 374 into the channel 354 and the pivot 356 is where the channel 354 reenters the lumen 374 proximate the other free end 392 of the positioning element.

Figure 17:
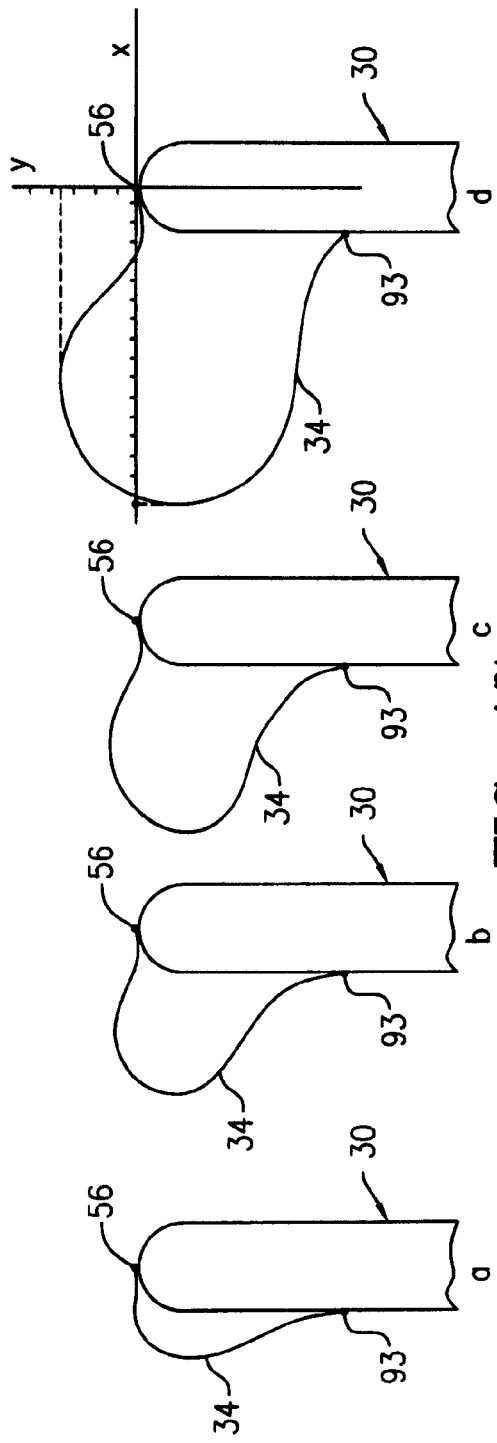
FIGS. 17a–d and 18a–d are diagrammatic sequential views of the deployment of a positioning element of two alternative embodiments of the present invention.
Figure 18:
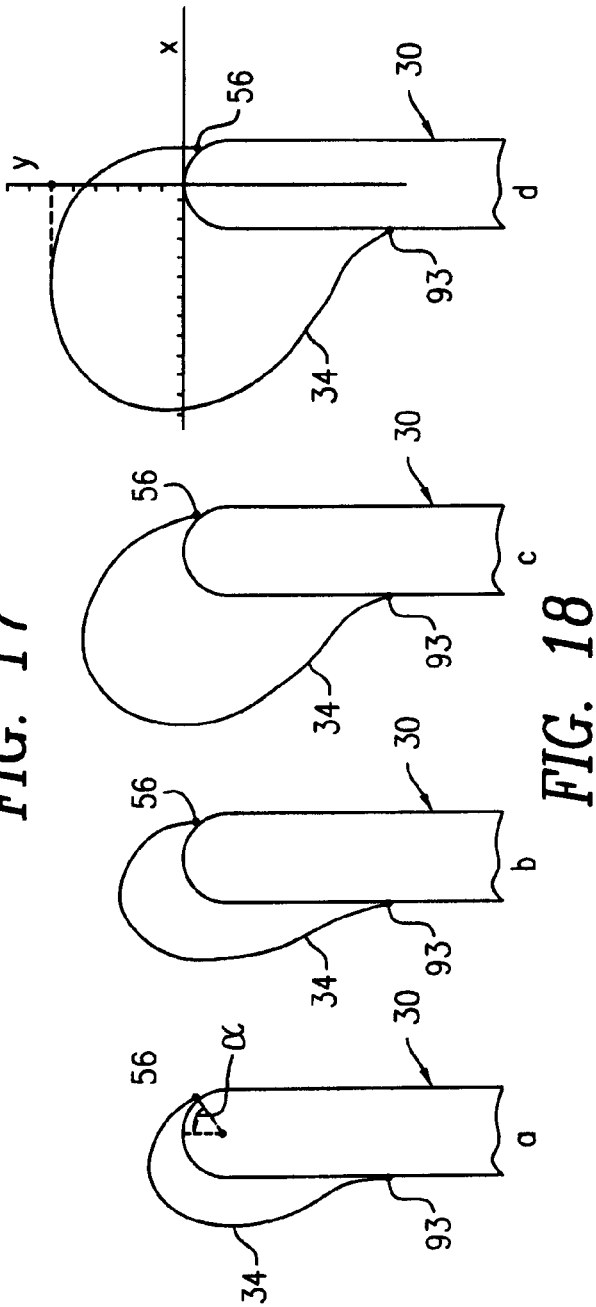

FIGS. 17 and 18 depict positioning element deployment shape in a sequence of progressions of increasing positioning element deployment. For simplicity, only one positioning element 34 is shown. An asymmetric or symmetrically displaced positioning element 35 could be deployed opposite to the positioning element 34 shown. In FIG. 17a–d, the pivot 56 is located centrally at the tip of the probe sheath 30. In this respect then, the positioning element shown in FIG. 17 deploys in the manner of the embodiment depicted in FIG. 3. When the pivot 56 is located centrally on the probe sheath 30 tip, the positioning element 34 tends to displace in an x direction, i.e., towards the fallopian tubes before displacing in the y direction, i.e., in the direction of the fundus. When fully deployed, as shown in FIG. 17d, it can be appreciated that the displacement in the x direction of the deployed shim is greater than its displacement in the y direction.

In FIG. 18, the pivot 56 is displaced from the center by angle α. This displacement results in a more even distribution of x and y displacement as the positioning element is deployed. Upon full deployment, the positioning element shown in FIG. 18d has approximately equal x and y displacements, i.e., displacements in the direction of the fallopian tubes and in the direction of the fundus. It can be concluded therefore that the pivot 56 displacement by angle α shown in FIG. 18 results in a greater cushioning effect of the tip and exerts a greater retrograde force that urges the tip away from the fundus. Given the potential for the cryoprobe to partially or completely penetrate the uterus through excessive forward travel under excessive force, the cushioning effect shown in FIG. 18 is desirable to prevent inadvertent penetration of the uterine wall.

Figure 19:
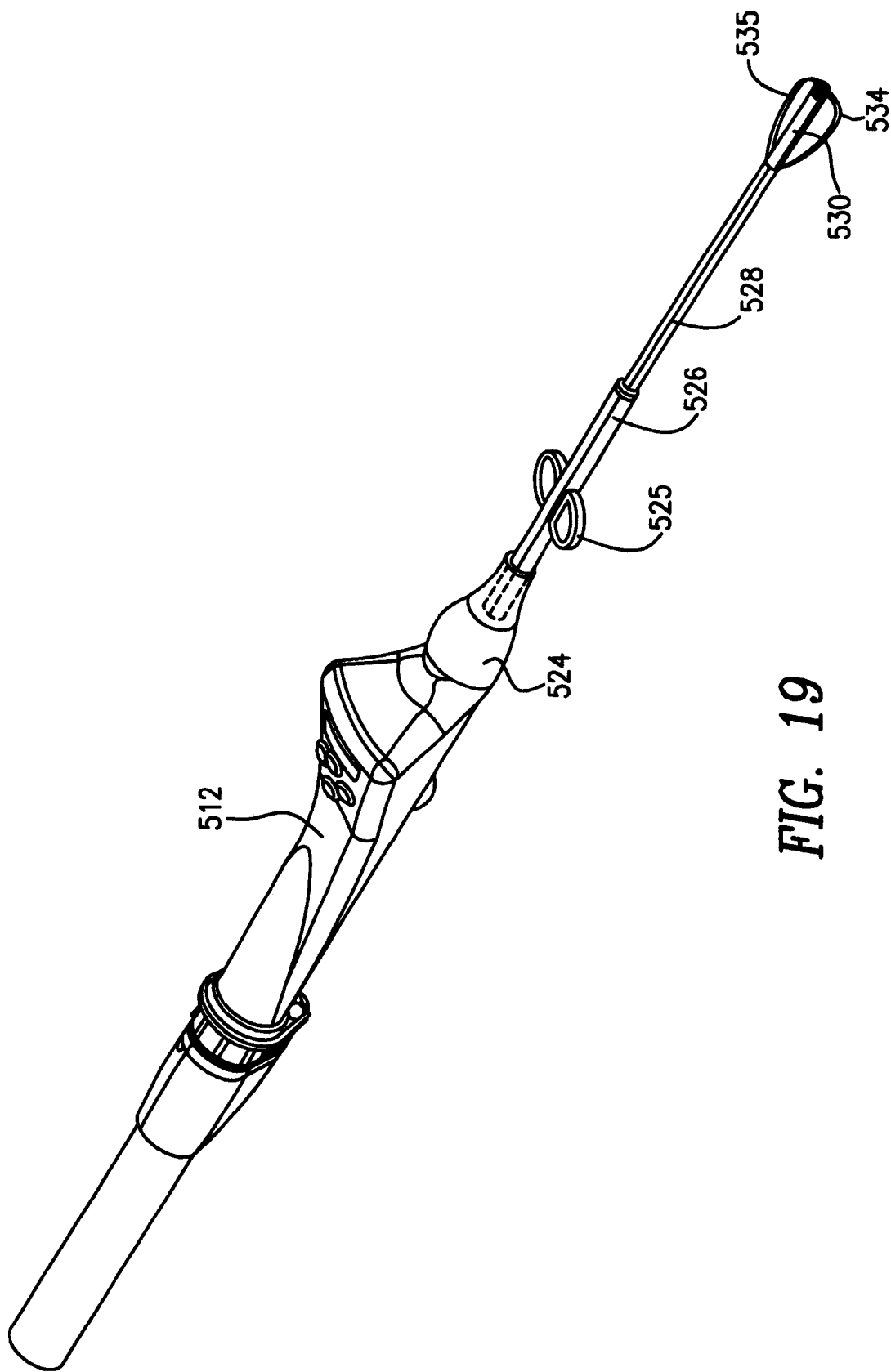
FIG. 19 is a perspective view of an alternative embodiment of a cryoprobe employing a positioning apparatus in accordance with the present invention.

FIG. 19 shows an alternative embodiment of the present invention wherein the intermediate shaft 526 and actuator tube 528 are split along one side permitting the intermediate shaft 526 and actuator tube 528 to be slipped over the probe sheath 530 laterally. The actuator tube 528 can be pushed forward to deploy the positioning elements 534 in order to position the cryoprobe within the uterus. Once centered, the cryoprobe can be activated to tack the tip in position in the uterus. When slid forward beyond the adaptor 524, the intermediate shaft 526 and actuator tube 528 can then be spread along the slit 527 by grasping the hand grips 525 and laterally slipped free of the sheath 530 to withdraw the intermediate shaft 526 and actuator tube 528 from the uterus and to withdraw the attached positioning elements 534 whose free ends are overlapped at the distal end of the probe sheath 530. In the embodiment shown in FIG. 19, the actuator tube 528 and intermediate shaft 526 simply slide telescopically on the sheath 530. An alternative actuating mechanism could be employed operating from a handgrip portion 512 and urging the intermediate shaft 526 forward to deploy the positioning elements 534, 535 either using a mechanical mechanism or under spring pressure as described above.

FIGS. 20–22 depict an alternative embodiment of the present invention utilizing a pair of positioning coils 635, 634 which are wound about an internal probe sheath 630. An exterior actuator tube 628 is attached to one end of each of the coils proximate the openings 611 in the actuator tube 628. The other end of each coil 634, 635 is attached to the probe sheath tube 630. When in a retracted position, the coils are tightly wound about the probe sheath 630 and do not protrude beyond the openings 611. When the apparatus is placed in the uterus, the exterior actuator tube 628 can be rotated relative to the interior probe sheath 630 thereby unraveling the shim coils 634, 635 causing them to protrude outwardly to accomplish the centering function. After the centering function has been accomplished, the coils 634, 635 may be retracted by rotating the probe sheath 630 in the reverse direction to recoil them to the retracted position. Alternatively, the actuator tube 628 may continue to be turned in the deploying direction which eventually will cause the wrapping of the coils 634, 635 about the probe sheath 630 and cause the free ends of the coils 634, 635 which are attached to the actuator tube 628 to be pulled from their retaining receptacles. This latter method of operation is also amenable to operation within a frozen thermal conductive medium in that the coils 634, 635 can be withdrawn along their own track through the solidified medium. Once the coils 634, 635 are withdrawn, the cryoprobe can be withdrawn from the uterus and the thermal transfer medium either in its liquefied or solidified state.

Figure 23:
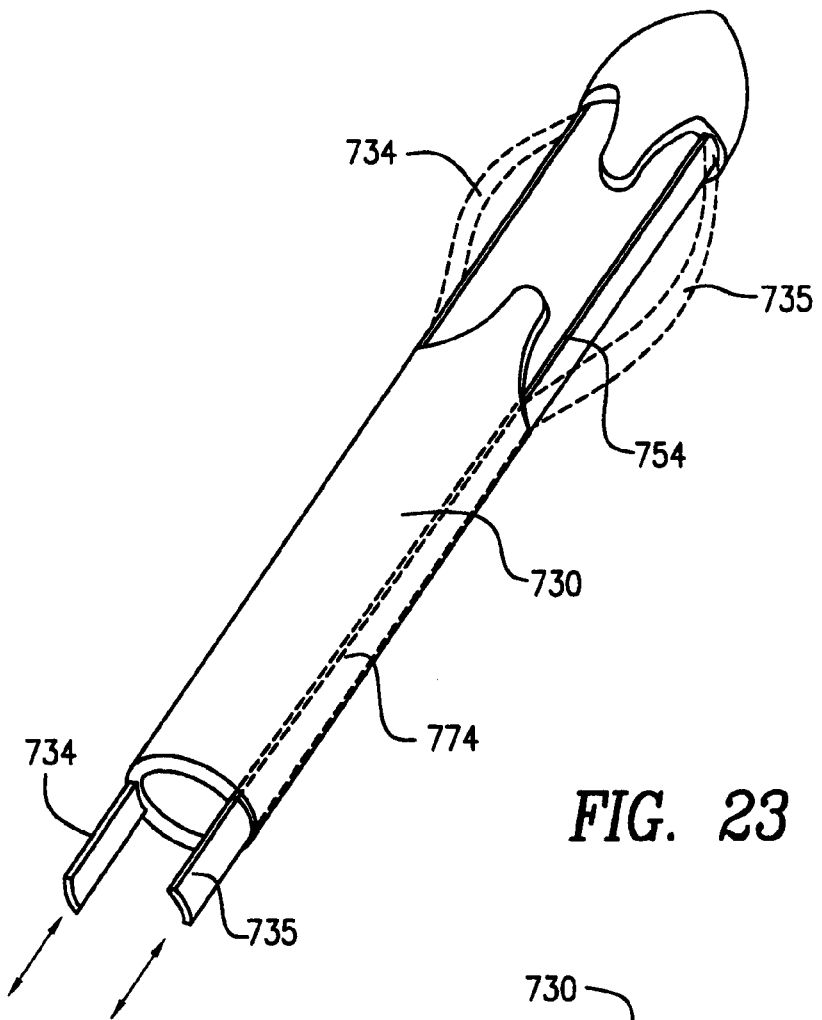
FIG. 23 is a fragmented perspective view of a cryoprobe tip sheath in accordance with an alternative embodiment of the present invention.
Figure 24:
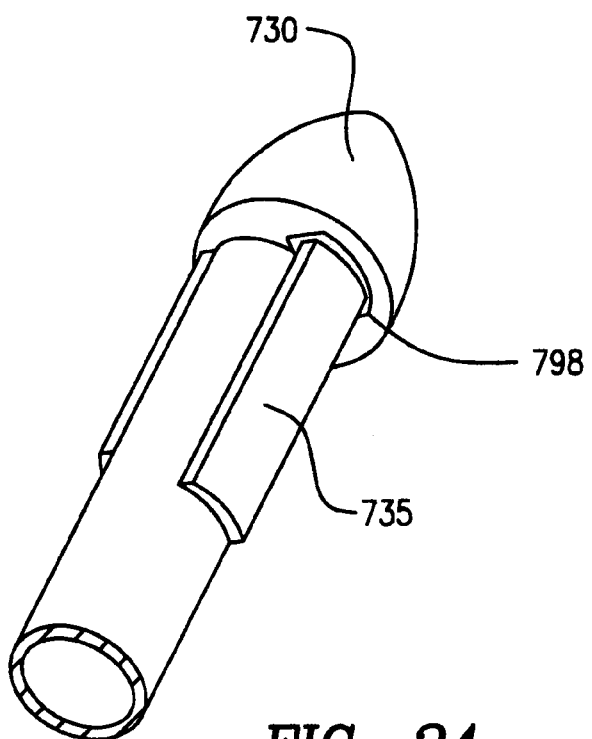
FIG. 24 is an enlarged view of the cryoprobe tip sheath of FIG. 23.

FIGS. 23 and 24 show an alternative embodiment of the present invention wherein positioning elements 734 and 735 pass through lumens 774 provided in the probe sheath 730. The lumens terminate at the upper end in channels 754 for receiving the positioning elements 734, 735 when in a retracted position such that the positioning elements do not extend above the surface of the probe sheath 730. FIGS. 23 and 24 are fragmented, with portions of the probe sheath 730 removed proximate the positioning elements 734, 735 to show their position in the retracted and deployed positions. FIG. 24 is an enlarged view of the distal tip portion of the sheath 730 showing positioning element retention holes 798 which receive the upper end of the positioning elements 735, 734 and permit the positioning elements to be withdrawn from the tip 730 after deployment and tacking or freezing of the thermally conductive medium. As can be seen, the receptacles 798 receive a free end of the positioning elements 734, 735 and thereby restrain the positioning element free end from pushing forward beyond the tip of the sheath 730 when the positioning element is pushed in the deploying direction. When retracted however, the free end of the positioning elements 735, 734 can be withdrawn from the receptacle 798.

FIGS. 25 and 26 show another alternative embodiment of the present invention wherein positioning elements 834 extend from an actuator tube 828 which is coaxially placed over the probe sheath 830 and is rotatable relative thereto. When in the undeployed position shown in FIG. 25, the positioning elements 834 are retained at their free ends proximate the tip of the sheath 830 in suitable retention holes 898. To deploy the positioning elements 834 and provide the centering function, the actuator tube 828 is rotated, uncoiling the positioning elements from their spirally wound position about the probe sheath 830. After the positioning function has been completed, i.e., either after the tacking of the probe sheath to the fundus or after the freezing process has been initiated to solidify the thermally conductive medium, the actuator tube 828 can then be withdrawn in a rearward fashion to pull the positioning elements 834 from their positions in the retention holes 898.

FIG. 27 shows an alternative embodiment wherein actuator tube 928 has a pair of pre-tensioned positioning elements 934, 935 having a relaxed shape which is biased outwards to perform the positioning function. In order to utilize the embodiment shown in FIG. 27, the positioning elements 934, 935 are pressed together and their ends are inserted in suitable receptacles 998 proximate the tip of the probe sheath 930 where they are retained during the placement of the cryoprobe. The positioning elements 934, 935 are deployed by withdrawing the actuator tube 928 rearwardly relative to the probe sheath 930 thereby freeing the ends of the positioning elements 934 and 935 from their receivers 998, 998 allowing the positioning elements to expand outwardly and to perform the positioning function.

Figure 28:
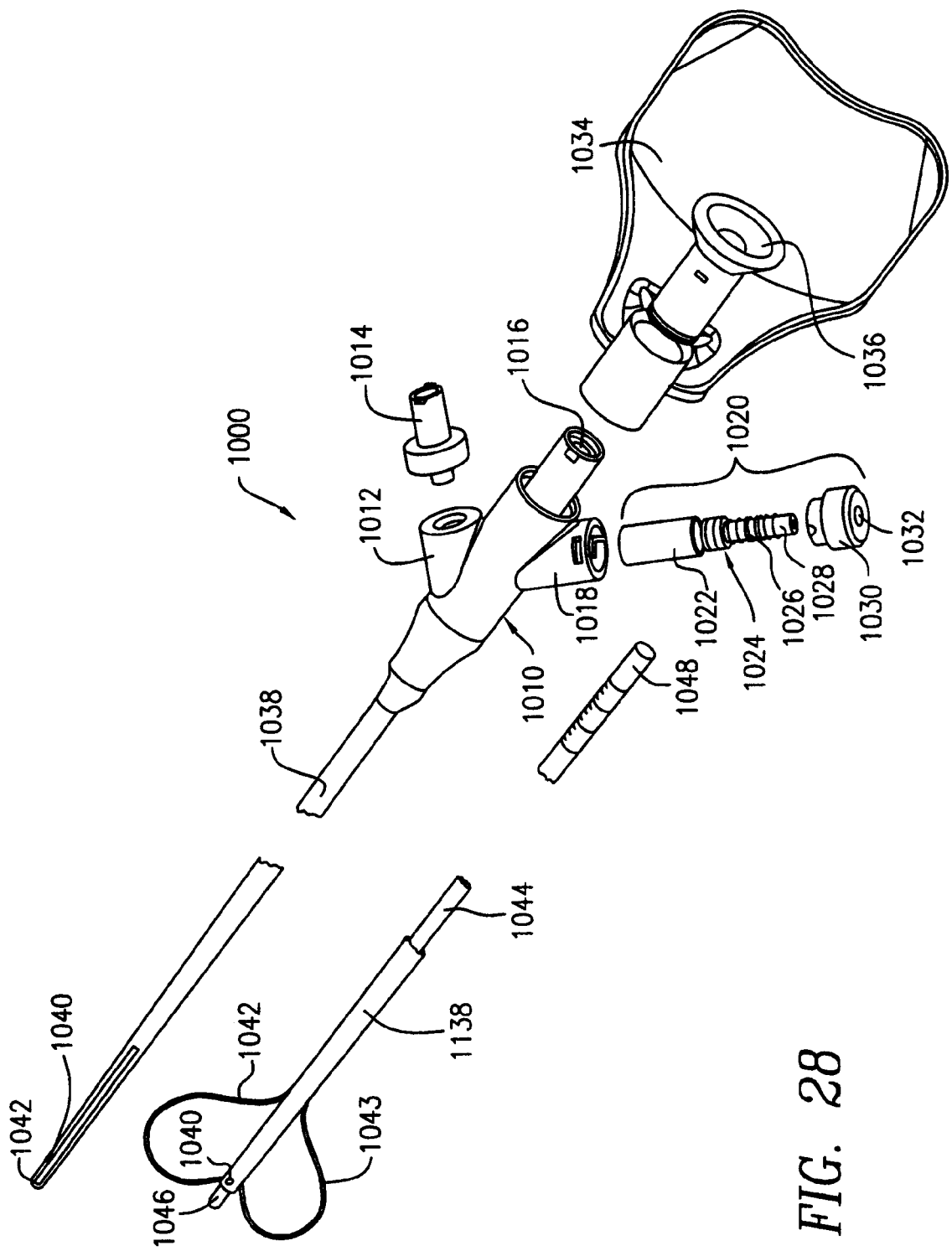
FIG. 28 is a partially exploded fragmented view of a cryoprobe guide and filler assembly for introducing a thermally conductive medium into a uterus.

FIG. 28 shows another aspect of the present invention, namely a probe guide and filler assembly 1000 which is used to introduce the thermally conductive medium into the uterus and to serve as a guide to a cryogenic probe. The guide and filler assembly 1000 depicted in FIG. 28 may employ a positioning assembly as described above, e.g., utilizing positioning elements 1042, 1043 that are deployed and retracted, or it may have an open distal end which permits a cryoprobe sheath having a positioning assembly thereon to be inserted through the guide tube 1138 for deployment of the centering apparatus.

When placing a catheter for infusing thermally conductive medium in the uterine cavity, it is essential to be able to determine whether the catheter has perforated the uterus. By distending the uterus with fluid under a given pressure using a limited amount of fluid, one can verify that the uterus is intact and has not been perforated. Measuring the pressure and volume of fluid introduced into the uterus can be used to determine that the introducing catheter has neither perforated the uterus nor has created a false passage by partially embedding itself into the uterine wall in that a perforated uterus would permit a larger volume of fluid to be infused at low pressure into the extra-uterine spaces of the body. In the instance of a partially penetrated uterine wall or false passage, a large amount of pressure would be ineffective to infuse even a small volume of thermally conductive fluid due to the fact that the fluid cannot pass into the uterine cavity and is plugged by its terminating in the uterine wall.

The probe guide and filler assembly 1000 operates upon the following principals. The volume of a normal uterus falls in the range between 6 and 30 mm. If one is not able to inject a minimum amount of fluid into the uterus, one can assume that a introducer fluid injection tube 1038 has created a "false passage" (it has been inserted to an intermediate depth into the intrauterine wall). By specifying a minimum amount of liquid at a maximum pressure one can test for false passage. On the other hand, if the uterus is perforated, the pressurized fluid can flow out the perforation. By specifying a maximum volume at a minimum pressure, one can use the present invention to test for a perforated uterus. The probe guide and filler assembly 1000 accomplishes this monitoring of volume and pressure and includes a multiport body 1010 having a fluid inlet port 1012 which includes a one-way check valve 1014. Inlet port 1012 communicates with a lumen extending down tube 1038 and terminating in outlet 1040. A pressure sensor port 1018 communicates with the fluid conduit extending between inlet 1012 and outlet port 1040. The pressure sensor port 1018 accommodates a pressure sensor assembly 1020 including a fluid pressure sensing piston 1022 and a plunger 1024 which receives a spring 1026 about a stem 1028 thereof. A cap 1030 with an opening 1032 is removably received within the pressure sensor port with the stem 1028 projecting through the opening 1032. Fluid pressure acting against the piston 1022 urges the plunger 1024 against the spring 1026 and causes the stem 1028 to project through the opening 1032 to varying degrees. The stem 1028 preferably has graduations marked thereon to quantify the pressure which the pressure sensor assembly 1020 indicates.

The multiport body 1010 also includes a central probe lumen 1016 for receiving a cryoprobe which may be provided with a check valve to prevent thermally conductive fluid from exiting the uterus through lumen 1016. A handle 1034 is utilized to assist in grasping the guide and filler assembly 1000 and includes a probe funnel 1036 to assist in introducing a cryoprobe into the probe lumen 1016. An elongated guide tube 1038 is utilized for introducing the guide and filler assembly 1000 into the uterus and has discharge outlet 1040 at one end through which the fluid medium is discharged. The tube 1038 may also include a positioning device in the form of positioning elements 1042, 1043 at the distal end thereof for positioning the apparatus in the uterus. In use, a syringe is filled with the specified thermally conductive fluid and is attached to the injection valve 1014. The syringe can then be depressed urging the fluid through the multiport body 1010 and through an associated lumen provided in the fluid delivery and guide tube 1038 which discharges from outlet port 1040 into the uterus. The pressure sensor 1020 is in communication with the lumen extending from the injection port 1012 to port 1040 in order to sense the pressure within that lumen as well as within the uterus. When the pressure sensor 1020 indicates a predetermined maximum pressure, a reading of the volume injected by the syringe can be made. If the volume injected falls within an acceptable range, one can infer that the guide and filler assembly 1000 has been safely placed within the uterine cavity and a suitable amount of thermally conductive medium introduced. Under certain circumstances, such as when the cervix has previously been dilated, it may be necessary to create a seal at the internal cervical os to prevent pressurized fluid from escaping around the probe at the cervix. This situation arises if the cervix has been dilated for the purpose of a hysteroscopic examination. A seal can be provided by a conventional balloon, elastic ring or cup disposed around the perimeter of the guide tube 1038 at a position where it would align with the cervical os. The use of a seal allows for the use of a less viscous fluid that fills the uterine cavity more easily and allows better pressure detection. The seal may operate internally to the cervix or externally.

After the guide and filler assembly 1000 has been employed to fill the uterus with a suitable quantity of thermally conductive medium, the cryoprobe can then be inserted through the lumen 1016 and cryogenic ablation can then be conducted. Alternatively, the cryoprobe can be inserted into the uterus through lumen 1016 prior to the infusion of thermally conductive media. As noted above, the guide and filler assembly 1000 can incorporate a positioning apparatus such as positioning elements 1042, 1043 that permit the assembly to be positioned correctly before initiation of the cryogenic procedure.

As yet a further alternative, a guide tube 1138 can have an open end to permit the passage of a sound 1046 and/or a cryoprobe. The open-ended version of the guide tube 1138 permits the use of a flexible sound 1044 with a soft tip 1046 and a calibrated end 1048 to be inserted into the uterus. Given that the distance from the opening at the tip of the guide tube 1138 to the opening in the cryoprobe funnel 1036 is a fixed distance, the sound 1044 which is inserted into the uterus can then serve as a guide for placing the guide and filler assembly 1000 into the uterus. The assembly 1000 may be inserted over a fully inserted sound 1044 starting at the calibration end 1048. The assembly 1000 is telescoped over the sound 1044 until it enters the uterus with the calibrated end 1048 protruding from the opening in the probe funnel 1036 where it assumes a predetermined depth of insertion relative thereto with the soft end 1046 protruding to some predetermined extent from the opening in the tip of the guide tube 1138. The flexible sound 1044 can then be removed and a cryoprobe inserted in its place in order to perform the cryogenic procedure. Accordingly, the present invention provides a complete system that can deliver the thermally conductive medium, seal the uterus, detect thermal fluid pressure and center the cryogenic probe for cryoendometrial ablation. The system can be operated with the single insertion of an outer sheath 1038 that has a discharge port 1040 through which the thermal fluid is ejected to fill the uterine cavity. Another port, i.e., the pressure sensor port 1018 on the assembly 1000 accommodates a pressure sensor 1020 and yet another port 1016 receives a cryoprobe. A positioning assembly 1042, 1043 may be incorporated on the guide tube 1038 or on the cryoprobe. The present invention also provides a method for positioning a cryoprobe in the uterus by mechanical means and without the use of an ultrasound, fluoroscope or any other external equipment.

The positioning mechanism can be removed either before the freezing cycle has begun, after tacking, or after freezing has been completed. The present invention permits the cryoprobe itself and any associated sheath to be removed after freezing and before the thermally conductive medium thaws. The positioning apparatus disclosed herein may be incorporated into the cryoprobe tip itself, a cryoprobe sheath, a guide and filler assembly or any other form of introducer tube or sound.

It should be understood that the embodiments described herein are merely exemplary and that a person skilled in the art may make many variations and modifications therein without departing from the spirit and scope of the invention. All such variations and modifications are intended to be included within the scope of the present invention as defined in the appended claims.

What is claimed is:

1. An apparatus for facilitating surgery within a body cavity using a cryoprobe having a proximal portion and a probe portion extending therefrom for insertion into the body cavity, comprising:

a positioning assembly for positioning a distal end of the probe portion within the body cavity at a selected position relative thereto, said positioning assembly having a positioning element which can assume a retracted position to allow insertion of said positioning assembly within the body cavity and a deployed position in which said positioning element is displaced radially outward relative to said retracted position and relative to an axis of the probe portion when the probe portion is inserted in the body cavity, said positioning element capable of contacting an interior surface of the body cavity to move the probe portion away from the interior surface when said positioning element is deployed;

a tubular probe sheath with a lumen and a blind distal end, said probe sheath adapted to accommodate the probe portion of the cryoprobe therein and supporting a distal end of said positioning element in the retracted and deployed positions;

an actuator for moving a proximal end of said positioning element relative to said probe sheath to deploy and retract said positioning element, said positioning element being in greater overall proximity to said probe sheath when in the retracted position to facilitate inserting said positioning assembly in the body cavity and diverging therefrom to a greater degree when in the deployed position.

2. The apparatus of claim 1, further including a plurality of positioning elements each of said distal ends thereof being free to disassociate from said probe sheath when pulled distally and each of said proximal ends thereof connected to said actuator, said actuator moving each of said proximal ends for deploying and retracting said positioning elements.

3. The apparatus of claim 2, wherein said positioning elements are positioned and shaped so as to cumulatively assume a substantially symmetric shape in the deployed position.

4. The apparatus of claim 2, wherein said positioning elements are positioned and shaped so as to cumulatively assume a substantially asymmetric shape in the deployed position.

5. The apparatus of claim 2, wherein said positioning elements are pre-tensioned to assume a deployed state when unconstrained, such that said actuator releases said shims to assume their relaxed shape to deploy said shims.

6. The apparatus of claim 2, wherein said positioning elements are laterally offset relative to each other.

7. The apparatus of claim 2, wherein said distal ends of said positioning elements overlap one another.

8. The apparatus of claim 2, wherein said positioning elements are spirally wound about said base member in the retracted position and are unwound to assume the deployed position.

9. The apparatus of claim 2, wherein said distal end of each of said positioning elements are inserted in a corresponding receptacle formed in said base member to allow said distal ends to be withdrawn from their corresponding receptacles when said positioning elements are pulled in a proximal direction relative to said base member.

10. The apparatus of claim 2, wherein said plurality of positioning elements are coiled about said base member in the retracted position and are uncoiled to assume the deployed position.

11. The apparatus of claim 1, wherein said probe sheath has a channel to receive said positioning element therein such that said positioning element does not protrude above the surface of said probe sheath when in the retracted position.

12. The apparatus of claim 11, wherein said channel terminates near said distal end of said probe sheath in a pivot, said positioning element passing beneath said pivot and being restrained by said pivot when deployed to prevent said positioning element from diverging from said probe sheath at said pivot.

13. The apparatus of claim 1, wherein said positioning element extends from said actuator to said channel by passing through a lumen in said probe sheath.

14. The apparatus of claim 1, further including an actuator tube interposed between said actuator and said positioning element, said proximal end of said positioning element being attached to said actuator tube, said actuator tube telescoping over said base member, said actuator urging a proximal end of said actuator tube in a distal direction to deploy said positioning element.

15. The apparatus of claim 1, wherein said positioning element is frangible at a point along its length.

16. The apparatus of claim 1, wherein said probe sheath has an open end that permits said cryoprobe surgical instrument to protrude through said open end.

17. The apparatus of claim 1, wherein said probe sheath has a longitudinal slit along its length to permit said probe sheath to be laterally removed from a cryoprobe inserted into said lumen.

18. The apparatus of claim 1, further including a deployment stop for restricting deployment travel of said positioning element to a selected degree.

19. The apparatus of claim 18, wherein said deployment stop has a plurality of settings for varying the extent of deployment.

20. The apparatus of claim 1, further including a resilient force limiting member interposed between said actuator and said positioning element, said force limiting member absorbing excess force that would otherwise be transferred to said positioning element when said positioning element encounters the interior surface of the body cavity.

21. The apparatus of claim 1, further including a resilient urging member for automatically urging said positioning element to the deployed position, said urging member having a selected potential energy for deploying said positioning element at a maximum selected force against the interior surface of the body cavity.

22. The apparatus of claim 1, wherein said positioning and assembly includes a cryoprobe having a pivot affixed at a distal end thereof, said positioning element threading under said pivot.

23. The apparatus of claim 1, wherein said positioning element is a wire.

24. The apparatus of claim 1, wherein said positioning element is coated with a polymer.

25. The apparatus of claim 1, wherein said positioning element is formed from tubular material.

26. The apparatus of claim 1, further including at least one thermocouple attached to said positioning element for ascertaining the temperature of said positioning element at a selected point along its length.

27. An apparatus for facilitating surgery within a body cavity using a cryoprobe having a proximal portion and a probe portion extending therefrom for insertion into the body cavity, comprising:

a positioning assembly for positioning a distal end of the probe portion within the body cavity at a selected position relative thereto, said positioning assembly having a positioning element which can assume a retracted position to allow insertion of said positioning assembly within the body cavity and a deployed position in which said positioning element is displaced radially outward relative to said retracted position and relative to an axis of the probe portion when the probe portion is inserted in the body cavity, said positioning element capable of contacting an interior surface of the body cavity and adapted to move the probe portion away from the interior surface when said positioning element is deployed;

a tubular probe sheath with a lumen and a distal end, said distal end of said probe sheath adapted to accommodate and axially restrain the probe portion of the cryoprobe therein; and an actuator for moving a proximal end of said positioning element relative to said probe sheath to deploy and retract said positioning element, said positioning element being in greater overall proximity to said probe sheath when in said retracted position to facilitate inserting said positioning assembly in the body cavity and diverging to a greater degree when in said deployed position; said positioning element being displaceable axially relative to the probe portion to move said distal end of said probe sheath and the probe portion away from the interior surface in an axial direction.

* * * * *